US010827935B2

(12) United States Patent
Qi

(10) Patent No.: US 10,827,935 B2
(45) Date of Patent: Nov. 10, 2020

(54) METHOD OF DETERMINING VIRTUAL HEPATIC VENOUS PRESSURE GRADIENT

(71) Applicant: Xiaolong Qi, Guangdong (CN)

(72) Inventor: Xiaolong Qi, Guangdong (CN)

(73) Assignee: Xiaolong QI, Guangdong (CN)

( * ) Notice: Subject to any disclaimer, the term of this patent is extended or adjusted under 35 U.S.C. 154(b) by 163 days.

(21) Appl. No.: 16/090,289

(22) PCT Filed: Nov. 25, 2016

(86) PCT No.: PCT/CN2016/107208
§ 371 (c)(1),
(2) Date: Jan. 8, 2019

(87) PCT Pub. No.: WO2017/173834
PCT Pub. Date: Oct. 12, 2017

(65) Prior Publication Data
US 2019/0117094 A1  Apr. 25, 2019

(30) Foreign Application Priority Data

Apr. 6, 2016 (CN) .......................... 2016 1 0211335

(51) Int. Cl.
*G06K 9/00* (2006.01)
*A61B 5/0215* (2006.01)
(Continued)

(52) U.S. Cl.
CPC .......... *A61B 5/02152* (2013.01); *A61B 5/021* (2013.01); *A61B 6/481* (2013.01);
(Continued)

(58) Field of Classification Search
CPC ..... A61B 5/02152; A61B 5/021; A61B 6/504; A61B 6/481; A61B 6/507; A61B 6/5217;
(Continued)

(56) References Cited

U.S. PATENT DOCUMENTS

| 2011/0003890 A1* | 1/2011 | Schwartz ............... A61K 33/30 514/491 |
| 2014/0136174 A1* | 5/2014 | Audigier ............ G06F 19/3481 703/11 |
| 2016/0084849 A1 | 3/2016 | Chojkier et al. |

FOREIGN PATENT DOCUMENTS

| CN | 103796579 A | 5/2014 |
| CN | 103976720 A | 8/2014 |

(Continued)

*Primary Examiner* — Dhaval V Patel
(74) *Attorney, Agent, or Firm* — Berggren LLP

(57) ABSTRACT

The present disclosure relates to the field of early non-invasive diagnosis, and specifically, to a method of determining a virtual hepatic venous pressure gradient. The method includes: constructing a 3-dimensional (3D) hepatic vein-portal vein model; establishing a finite element division mathematical model; and applying fluid dynamics to compute and simulate a virtual hepatic venous pressure gradient (vHVPG). The method optimizes and improves a more complete 3D hepatic vein-portal vein model, finite element division, and fluid dynamic simulation computation, constructing and validating a new vHVPG determination technology providing better diagnosis, providing a safe, non-invasive, accurate, and quantitative method for early non-invasive diagnosis of a portal vein high pressure patient.

2 Claims, 39 Drawing Sheets

(51) Int. Cl.
  *G06T 19/00* (2011.01)
  *A61B 5/021* (2006.01)
  *A61B 6/00* (2006.01)
  *G16H 30/40* (2018.01)

(52) U.S. Cl.
  CPC .............. *A61B 6/504* (2013.01); *A61B 6/507* (2013.01); *G06T 19/00* (2013.01); *A61B 6/5217* (2013.01); *G06T 2210/41* (2013.01); *G16H 30/40* (2018.01)

(58) Field of Classification Search
  CPC ..... G06T 19/00; G06T 2210/41; G06T 19/20; G16H 30/40; G16H 50/20; G16H 50/50
  See application file for complete search history.

(56) References Cited

FOREIGN PATENT DOCUMENTS

| | | |
|---|---|---|
| CN | 104107039 A | 10/2014 |
| CN | 105825070 A | 8/2016 |
| WO | 2010063676 A | 6/2010 |

\* cited by examiner

METHOD OF DETERMINING VIRTUAL HEPATIC VENOUS PRESSURE GRADIENT

CROSS-REFERENCE TO RELATED APPLICATIONS

The present application is a continuation-in-part application based on PCT Application No. PCT/CN2016/107208 flied on Nov. 25, 2016 and entitled "Method of Determining Virtual Hepatic Venous Pressure Gradient", which claims priority to the Chinese patent application No. CN2016102113357, filed with the Chinese Patent Office on Apr. 6, 2016, the contents of which are incorporated herein by reference in their entirety.

TECHNICAL FIELD

The present disclosure relates to the field of early non-invasive diagnosis, and particularly to a method for determining a virtual hepatic venous pressure gradient.

BACKGROUND ART

Liver diseases (viral infection, alcoholic liver disease, nonalcoholic fatty liver disease and related liver cirrhosis, and hepatocellular carcinoma) are one of the main causes of death all over the world. Liver diseases threaten the health and life of nearly 300 million people only in China, and severely increase the burden of diseases all over the world. Taking chronic liver diseases caused by hepatitis B virus infection as an example, according to the report from the World Health Organization, about 2 billion people in the world have ever been infected with hepatitis B virus, among which 240 million people are infected with chronic hepatitis B virus. Each year, about 650,000 people die from liver cirrhosis, hepatocellular carcinoma, etc., caused by hepatitis B virus infection. Among people suffering from liver cirrhosis worldwide, 30% are caused by hepatitis B virus infection. In China, the proportion of liver cirrhosis caused by hepatitis B virus infection is as high as 60%. Therefore, the high incidence and poor clinical outcome of liver cirrhosis have caused serious social public health problems at home and abroad.

Portal hypertension is one of the important manifestations of decompensation stage of liver cirrhosis. Since it is asymptomatic, clinically, portal hypertension is often discovered and diagnosed due to the occurrence of severe late complications, such as acute variceal bleeding, refractory ascites, hepatic encephalopathy, portal hypertensive gastroenteropathy, hepatorenal syndrome, hepatopulmonary syndrome, secondary infection. Therefore, portal hypertension and its complications seriously affect the quality of life and long-term prognosis of people suffering from liver cirrhosis. The diagnosis and monitoring of portal hypertension (especially early asymptomatic portal hypertension) are one of the most important parts in the chain of the treatment of end-stage liver diseases such as liver cirrhosis.

In the latest 2015 version of the Baveno VI Consensus Workshop (Stratifying risk and individualizing care for portal hypertension), the determination of invasive hepatic venous pressure gradient (HVPG) is continued to be recommended as the gold-standard method for diagnosing clinically significant portal hypertension, which is defined as HVPG≥10 mmHg (de Franchis R #*, Baveno VI Faculty. Expanding consensus in portal hypertension: Report of the Baveno VI Consensus Workshop: Stratifying risk and individualizing care for portal hypertension. J Hepatol. 2015; 63(3):743-752.). In the invasive method, a catheter is placed by internal jugular vein puncture, the catheter sequentially passes through internal jugular vein, superior vena cava, right atrium, inferior vena cava and enters hepatic vein to determine free hepatic venous pressure (FHVP) and wedged hepatic venous pressure (WHVP), and HVPG is obtained by calculating the deviation value therebetween [Bloom S #, Kemp W, Lubel J*. Portal hypertension: pathophysiology, diagnosis and management. Intern Med J. 2015; 45(1):16-26.]. In addition, HVPG may also provide important information for therapeutic response, risk of complications and long-term prognosis, and change in its numerical value is recommended as a surrogate marker for the study of prognosis. Furthermore, HVPG determination is also encouraged to be used in clinical trials to study innovative diagnostic and therapeutic approaches to portal hypertension. However, there are also some problems in HVPG determination, firstly, the means of determination is invasive, and thus it can hardly be accepted by the patients in the early stage of portal hypertension when there is no serious complication; secondly, the determination needs to be carried out by a professionally trained interventionalist with the assistance of hepatic venography, which not only increases the possibility of radiation exposure and allergy of contrast agent of the subjects, but also has certain risk in technical operations; in addition, the cost of diagnosis is high. As a result, HVPG determination is severely limited in China, and is available only in some upper first-class hospitals at present. In addition, invasive diagnostic techniques of portal hypertension further include: ultrasound-guided portal vein puncture pressure measurement and direct portal venous pressure measurement during laparotomy [de Franchis R #*, Dell'Era A. Invasive and noninvasive methods to diagnose portal hypertension and esophageal varices. Clin Liver Dis. 2014; 18(2): 293-302.]. However, direct measurement of portal venous pressure is riskier and imposes higher requirements on the skill level of the operator, which can hardly be accepted by both doctors and patients in clinical practice and is still mainly used in animal experimental studies at present.

The non-invasive assessment of portal venous pressure is an important part of the studies in this field at present, which mainly includes the following three aspects. (1) Detection of intrahepatic resistance: the increase of intrahepatic resistance is an important factor of the formation of portal hypertension. The release of endogenous vasoconstrictive substance and the disorder of liver tissue structure may contribute to a significant increase in intrahepatic resistance. Some studies suggest that there is a correlation between the expression of serum endothelin-1 and HVPG, but this conclusion still lacks the support of clinical trials with large sample size. Moreover, the change of intrahepatic mechanical structure will also lead to an increase in intrahepatic resistance. In clinic, the technique of FibroScan is widely used to assess the degree of liver cirrhosis via determination of liver hardness value. The method is easy to operate and has good reproducibility. However, it has also been reported that the diagnostic accuracy of FibroScan is interfered by obesity, intercostal stenosis, inflammation and other factors, which does not have high value for predicting the portal hypertension complications (such as high-risk esophageal varices), and needs to be combined with other non-invasive indexes for comprehensive judgment. (2) Determination of the portal vein circulation blood volume: the direct factor of portal hypertension is that the accumulation of circulation blood volume exceeds the compensation of the body, and when liver cirrhosis is accompanied with severe portal hypertension, the cardiac output will increase obviously and have a high correlation with HVPG. In some studies, color Doppler ultrasound (CDUS) has been used to determine the portal vein diameter and blood flow velocity in patients with liver cirrhosis, and on this basis, the circulation blood volume of portal vein system is calculated. However, the CDUS determination technique is relatively more subjective and susceptible to be interfered by factors such as obesity, and there is no accurate clinical evidence demonstrating that the portal venous pressure calculated through blood flow velocity and portal vein diameter has high diagnostic consistency with HVPG. In addition, CT angiography (CTA) and magnetic resonance venography can also be used to assess the circulation blood volume in the portal vein system. However, the determination principle is still indirect evaluation of portal venous pressure based on the portal vein diameter and collateral circulation. (3) Simulation calculation of portal venous pressure: virtual simulation technology is the result of intercrossing and combination of computer graphics, medical image processing, software engineering calculation and other disciplines. Virtual human body data obtained by computer simulation assisted medical imaging provides a new idea for the interventional diagnosis and treatment of diseases. At present, a number of international prospective clinical trials have shown that the fractional flow reserve based on CTA and fluid dynamics calculation is of high diagnostic value for coronary artery functional stenosis, and the relevant simulation calculation software has also been approved by the U.S. Food and Drug Administration.

At present, the various determination techniques of portal venous pressure are still affected by their respective interference factors, either being invasive and highly risky and having high operation difficulty, or being affected by many factors and having large variations in numerical values. In addition, the main problems of the studies in this field at home and abroad further lie in: the range of assessment is limited to the main portal vein, without taking account of the overall impact of the hepatic vein-portal vein system; and only the portal vein hemodynamic factors are considered, the hemorheological changes in patients with liver cirrhosis are neglected, e.g., the change in blood viscosity and the decrease of erythrocyte deformability can both cause the increase of portal resistance.

In the current relevant domestic and foreign reports, the diagnostic methods of portal hypertension, especially the techniques of early non-invasive diagnosis, still need to be further studied and improved.

SUMMARY

An object of the present disclosure is to provide a method for determining virtual hepatic venous pressure gradient, based on which a new technique for determining virtual hepatic venous pressure gradient that is more diagnostically advantageous can be constructed, so as to provide a new approach to early non-invasive diagnosis for patients with portal hypertension.

The method for determining virtual hepatic venous pressure gradient according to the present disclosure comprises the following steps:

A. injecting a contrast agent through the median cubital vein of a specimen, performing CT angiography (CTA) to acquire CTA slice sequence including hepatic venous phase, and exporting the slice sequence, with the format of dicom, a slice thickness of 1.25 mm and an image resolution of 512×512 pixels;

B. importing the acquired CTA slice sequence into the medical image control software MIMICS, selecting the hepatic venous phase slice sequence, setting the orientation of the image sequence, and automatically recognizing the image sequence by the MIMICS software to generate coronal, sagittal and horizontal images of the hepatic venous phase CTA image sequence;

C. searching for the hepatic vein-portal vein system (target) in the image, and setting a threshold range by using the Thresholding tool (threshold algorithm based on Hounsfield units) of MIMICS software with the principle of including the CT value of the target and excluding the CT values of the surrounding liver parenchyma and other soft tissues as much as possible, so as to extract the target; further extracting the target structure and eliminating non-target structures by using Crop mask tool of the MIMICS software; selecting the target using the Region growing tool of the MIMICS software so as to only extract a structure connected with the target in spatial structure; and establishing a preliminary 3D hepatic vein-portal vein model by using the Calculate 3D from mask (3D modeling) tool of the MIMICS software and selecting quality to be medium (medium precision);

D. eliminating the residual non-target structures and only retaining the hepatic vein-portal vein system by using the Edit masks in 3D tool of the MIMICS software; and further selectively filling the hepatic vein-portal vein system and eliminating noise pixels by repeatedly using the Edit masks in 3D (3D cutting) tool and the Edit mask (2D edit mask) tool of the MIMICS software, so as to reconstruct a solid 3D model of hepatic vein-portal vein system with the lumen being closed;

E. reducing the node and smoothing the surface of the 3D model using the Remesh tool of the Finite element analysis of the MIMICS software;

F. importing the area element (with the format .lis) in the classic mode of ANSYS, and unifying the unit of length as the international unit m; and establishing a solid model of hepatic vein-portal vein system model on the basis of area;

G. making a vertical section of the blood inlet and outlet of the hepatic vein-portal vein system model by Boolean operation, to obtain an open geometric model of the virtual free hepatic venous pressure (vFHVP); and thereafter exporting the file with the suffix .IGS for use (IGS is a file format of 3D numerical model, which is readable by the ANSYS Workbench module);

H. establishing an ANSYS Workbench finite element calculation platform, including a geometrical model module Geometry, a fluid calculation module Fluent and a Results module (i.e., CFD-POST post-processing module), importing the IGS file through the Geometry module, in a Mesh unit, the objects of meshing being imported numerical models and the meshing method being set as Tetrahedrons; selecting CFD (Computational Fluid Dynamics) in Physics Preference, and selecting Fluent in Solver Preference (solving the flow field using Fluent); defining the mesh size in consideration of the operation accuracy and the computer running speed, setting the max face size to 1.5 mm and the max size to 4 mm; thereafter accomplishing meshing through Generate Mesh;

I. setting material parameters (blood density, blood viscosity, blood vessel wall density) in solution of the fluid dynamics calculation module Fluent to make the physical properties of the model close to the biological properties of human body so as to improve the accuracy of simulation; solving control parameters (calculating the step size, the number of iterations, the maximum number of cycles) and boundary conditions (naming the blood inlet surface and providing therefor a velocity value, naming the outlet surface and then providing therefor a pressure value, and setting an unnamed blood vessel wall as wall), the Reynolds number of portal vein flow being Rε<2000, so the simulation fluid being set as a laminar flow; setting the operation initialization to start from the inlet surface; and simulating the fluid-solid coupling between the blood vessel wall and the blood after the completion of the parameter setting described above, and obtaining, by calculation, the pressure distribution and blood flow distribution of the simulation 3D blood vessel model;

J. constructing a panel for virtual free hepatic venous pressure (vFHVP) in the results post-processing module; reading the results and displaying the pressure distribution map of the liver-portal vein model through contour operation; and acquiring, by calculation, the numerical value of the vFHVP by using the calculators tab provided by the software;

K. creating a cylinder with a diameter greater than or equal to that of the truncated blood vessel to simulate an occlusion sacculus, blocking the right hepatic vein by Boolean operation to obtain an open geometric model of the virtual wedged hepatic venous pressure (vWHVP), and exporting the same as an IGS file for use (referring to step F); importing the IGS file into the ANSYS workbench, endowing the generated two sections with a velocity of 0 m/s to simulate blood flow stasis and keeping the other material parameters, boundary conditions and solution control parameters unchanged, thereby obtaining, by calculation, the virtual wedged hepatic venous pressure (vWHVP), and reading the virtual wedged hepatic venous pressure (vWHVP) in the results module;

L. calculating the deviation value between the vWHVP and the vFHVP, which is just the virtual hepatic venous pressure gradient (vHVPG).

According to a further feature of the method for determining a virtual hepatic venous pressure gradient according to the present disclosure, in step I, the material parameters are set as follows: blood density=1050 kg/m³, blood viscosity=0.005 kg/m·s, and blood vessel wall density=1150 kg/m³.

As mentioned above, the definite clinical diagnosis of portal hypertension, which is an important feature of decompensation stage of liver cirrhosis, often lags the occurrence of severe late complications. At present, the diagnostic techniques of portal hypertension at home and abroad are either invasive and highly risky and have high operation difficulty, or are affected by many factors and have large variations in numerical values. The present disclosure has proposed, for the first time, the concept of virtual hepatic venous pressure gradient (vHVPG), and obtained important data in the methodological construction thereof, which is beneficial to exploring and establishing a safe, non-invasive, accurate and quantitative diagnostic technique of portal hypertension. The present disclosure optimizes and improves 3D modeling of hepatic vein-portal vein system, finite element meshing and fluid dynamics simulation calculation, constructs and verifies a new vHVPG determination technique that is more diagnostically advantageous, and provides a new approach to the early non-invasive diagnosis for patients with portal hypertension.

DETAILED DESCRIPTION OF EMBODIMENTS

Below, the present disclosure is described in detail with reference to the drawings.

The method for determining virtual hepatic venous pressure gradient (vHVPG) according to the present disclosure comprises: constructing a 3D hepatic vein-portal vein model; establishing a finite element meshing mathematical model; and obtaining a vHVPG via fluid dynamics simulation calculation.

Figure 1:
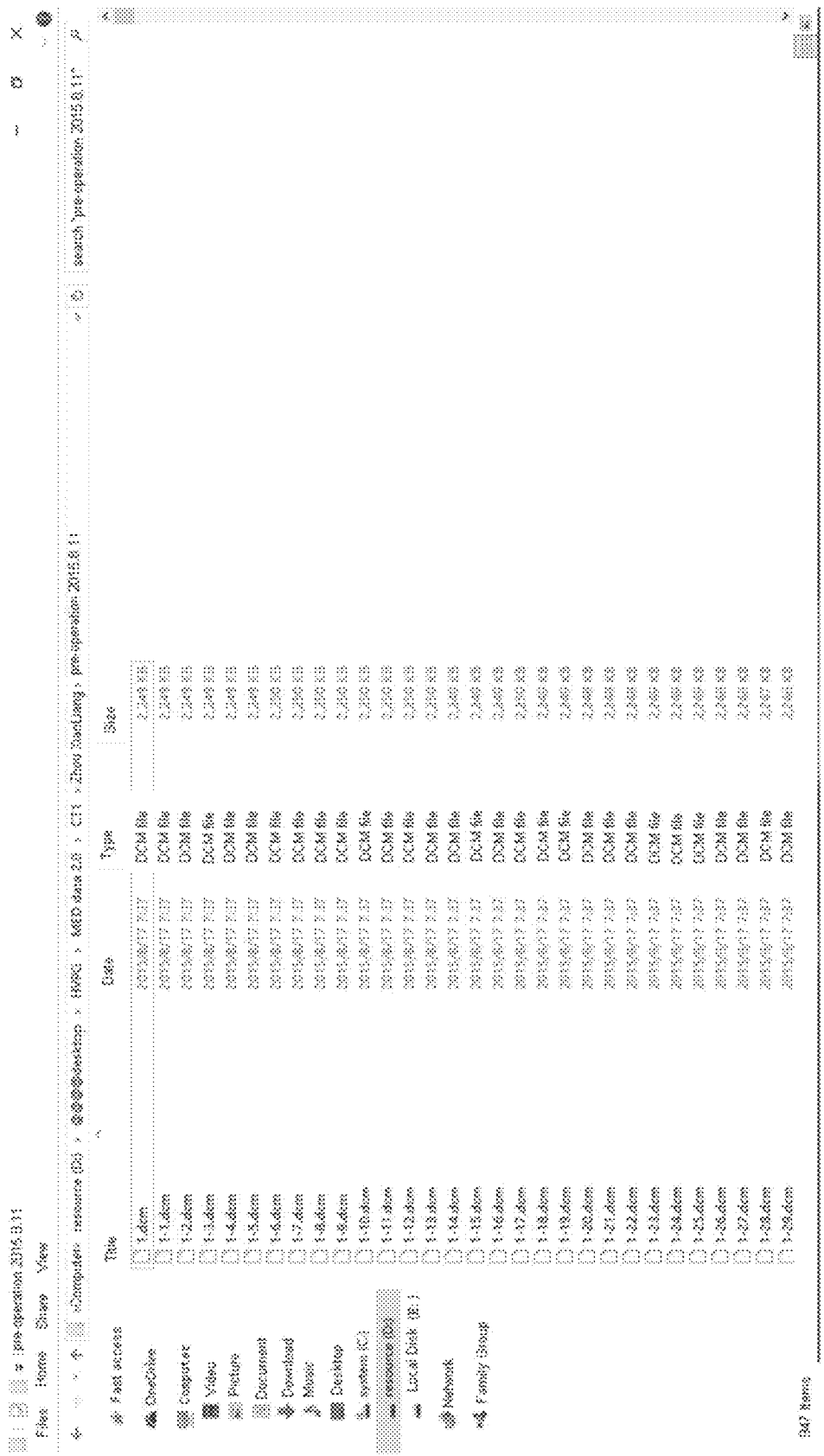
FIG. 1 shows a CTA slice sequence including hepatic venous phase exported from CT angiography (CTA).

1. A contrast agent is injected through the median cubital vein of a specimen, CT angiography (CTA) is performed to acquire CTA slice sequence including hepatic venous phase, and the slice sequence is exported, with the format of dicom, a slice thickness of 1.25 mm and an image resolution of 512×512 pixels, as shown in FIG. 1.

Figure 2:
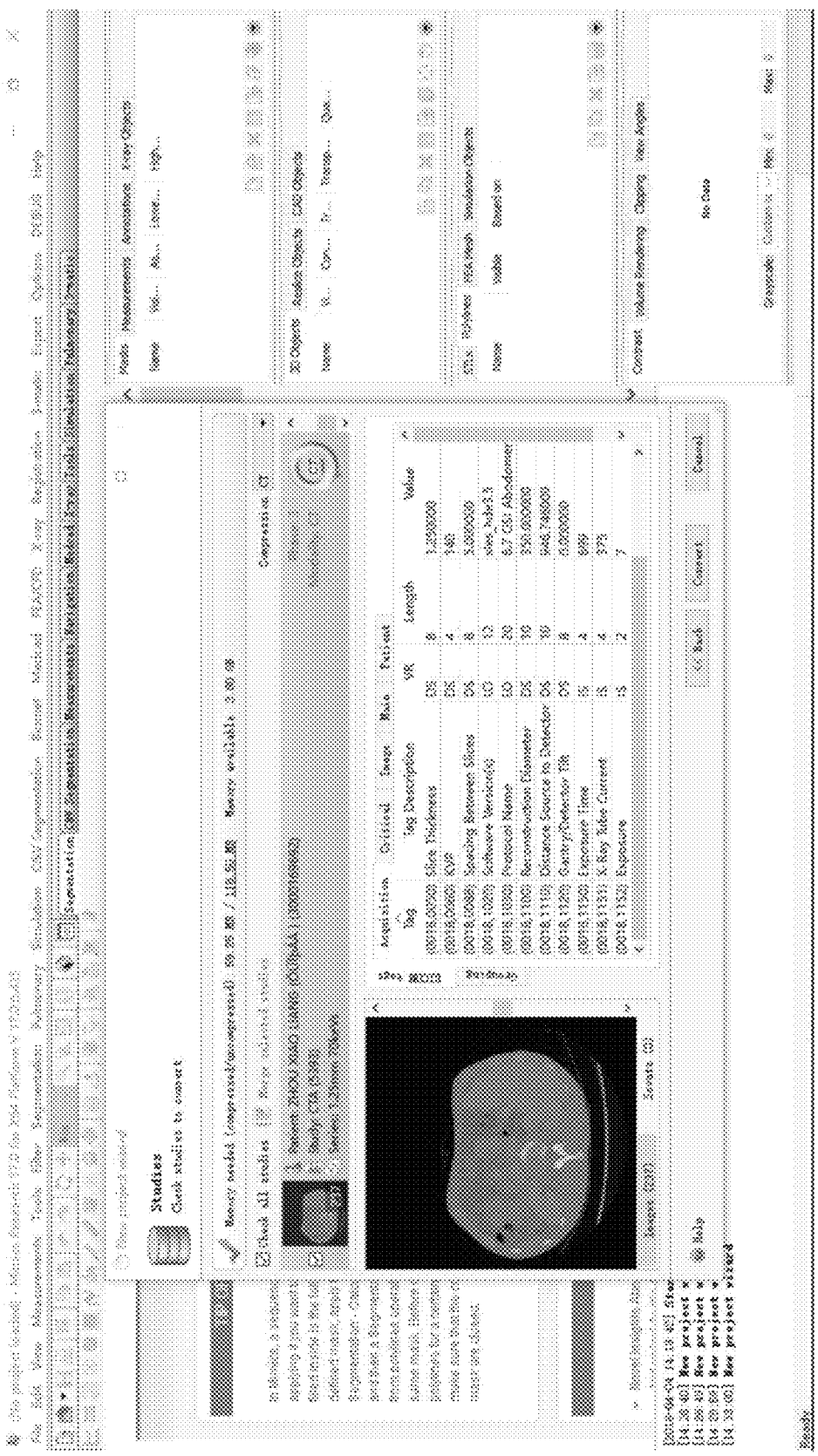
FIG. 2 shows a hepatic venous phase CTA slice sequence selected to be imported, with a slice thickness of 1.25 mm.
Figure 3:
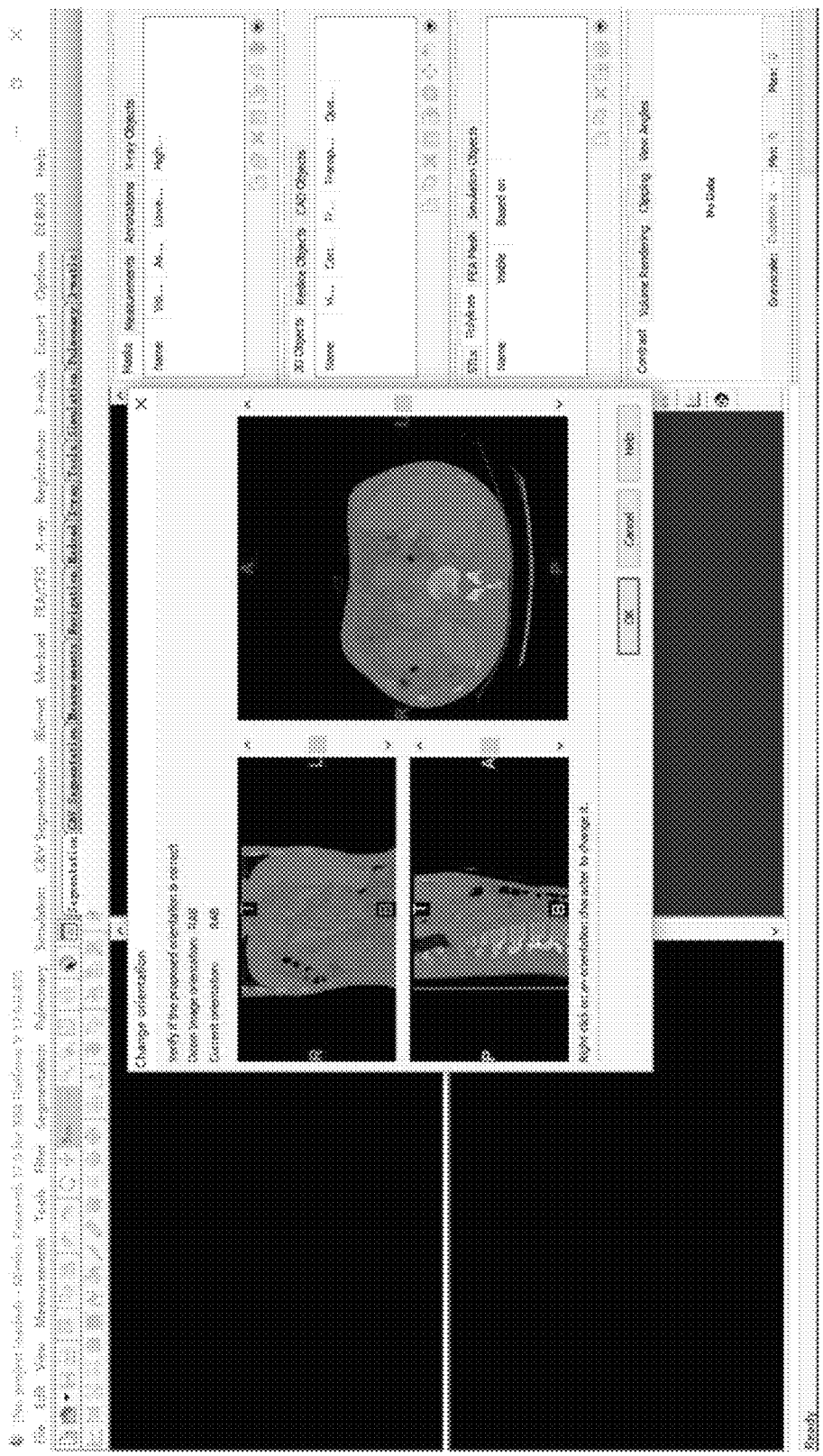
FIG. 3 shows setting of the orientation of the slice sequence.
Figure 4:
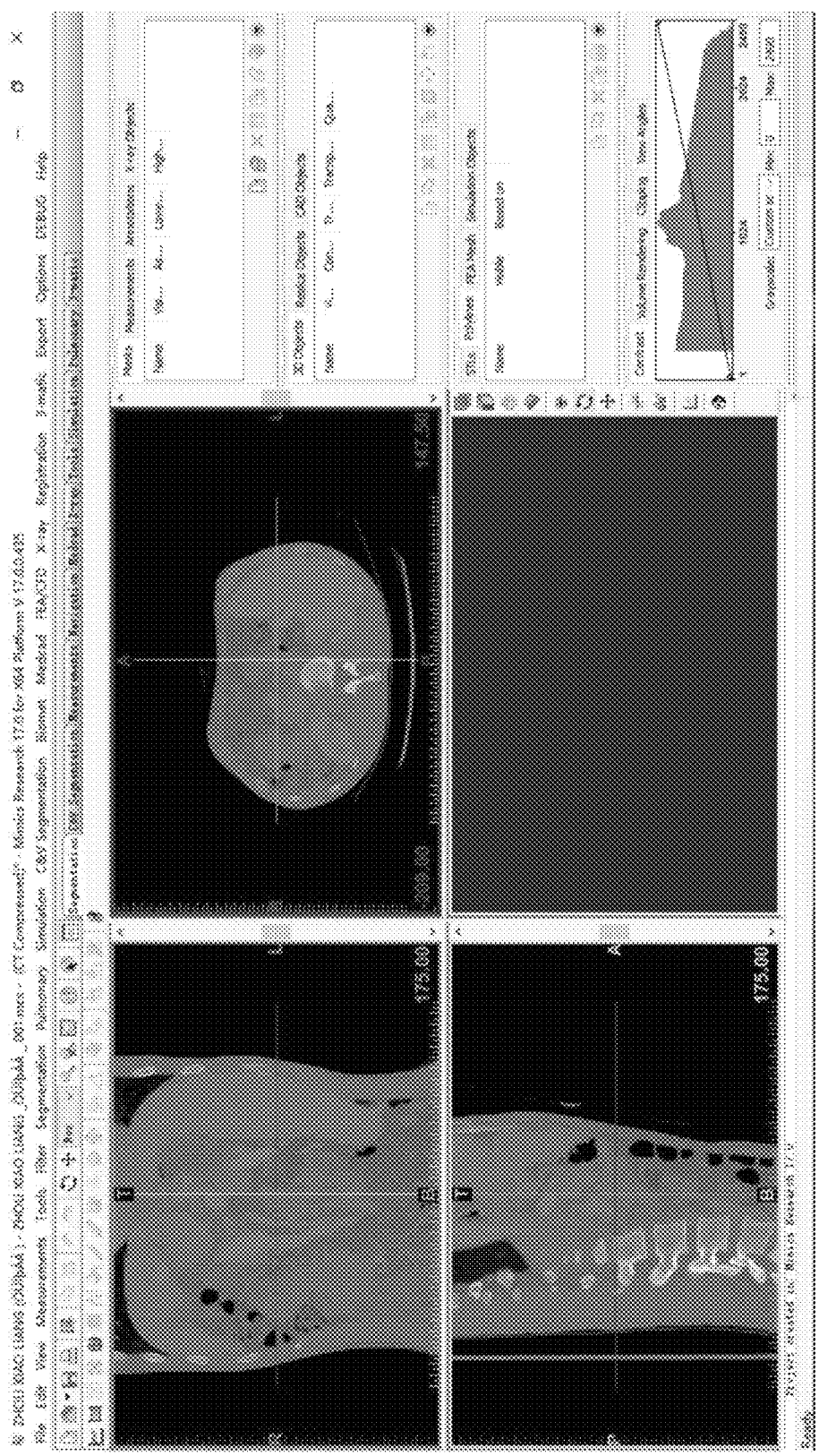
FIG. 4 shows automatically generated coronal, sagittal and horizontal images.

2. The acquired CTA slice sequence is imported into the medical image control software MIMICS, the hepatic venous phase slice sequence is selected (as shown in FIG. 2), the orientation of the image sequence is set (as shown in FIG. 3), and the MIMICS software automatically recognizes the image sequence to generate coronal, sagittal and horizontal images of the hepatic venous phase CTA image sequence (as shown in FIG. 4).

Figure 5:
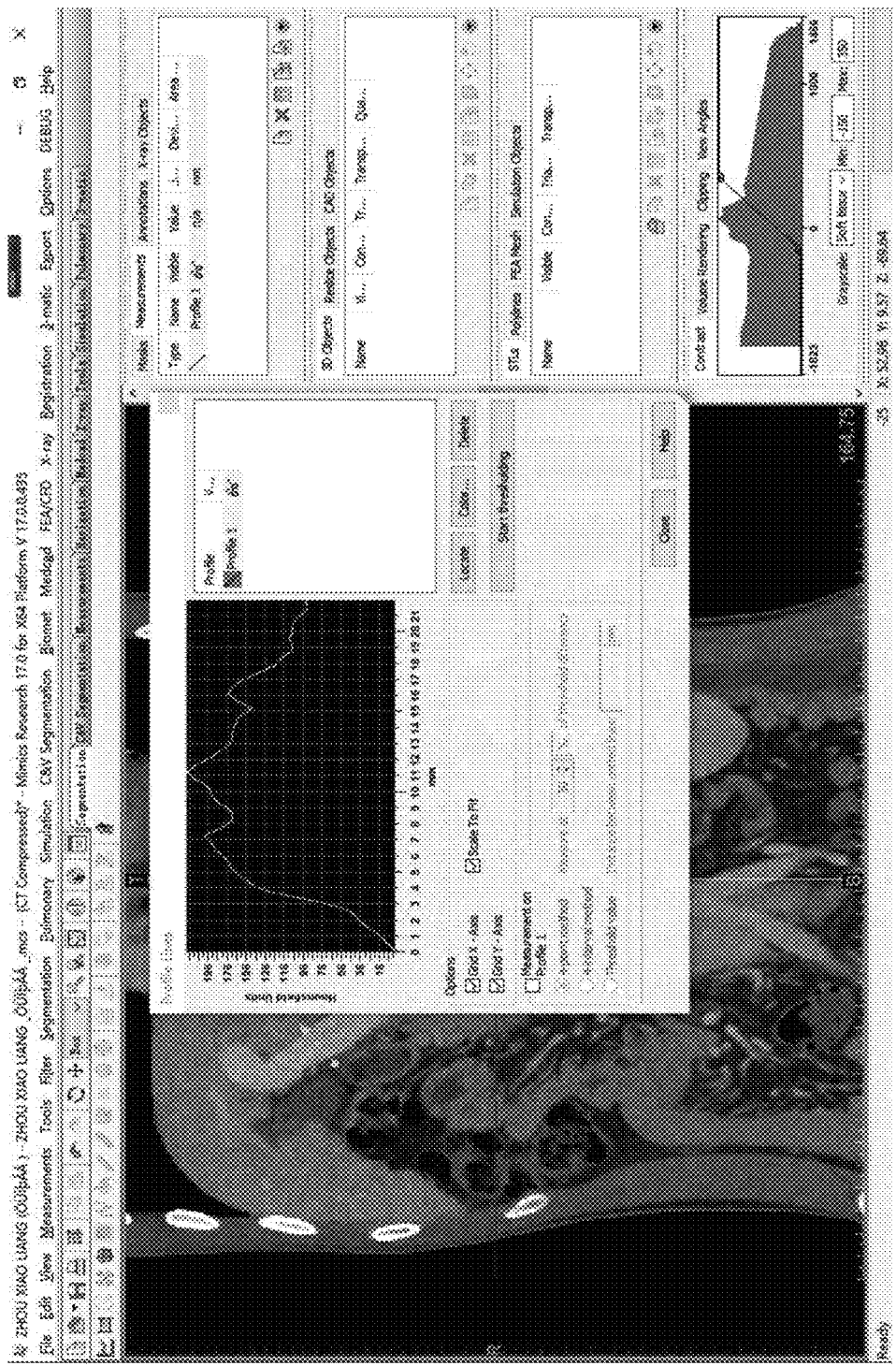
FIG. 5 shows locating of the portal vein, and selecting of the range of appropriate CT values according to the change of the CT value of the portal vein across the green arrow.
Figure 6:
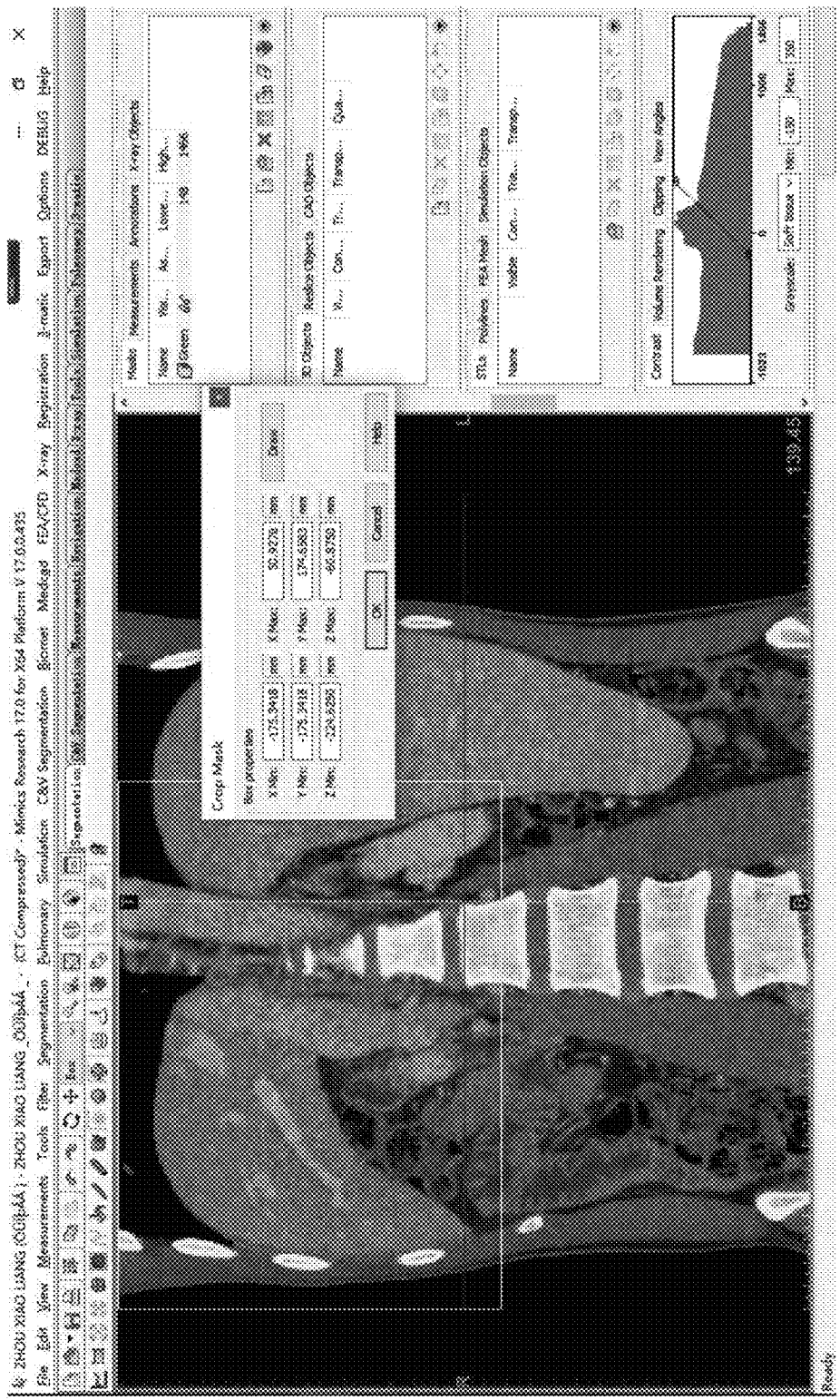
FIG. 6 shows removing of the selected area besides the liver-portal vein as much as possible by using Crop mask.
Figure 7:
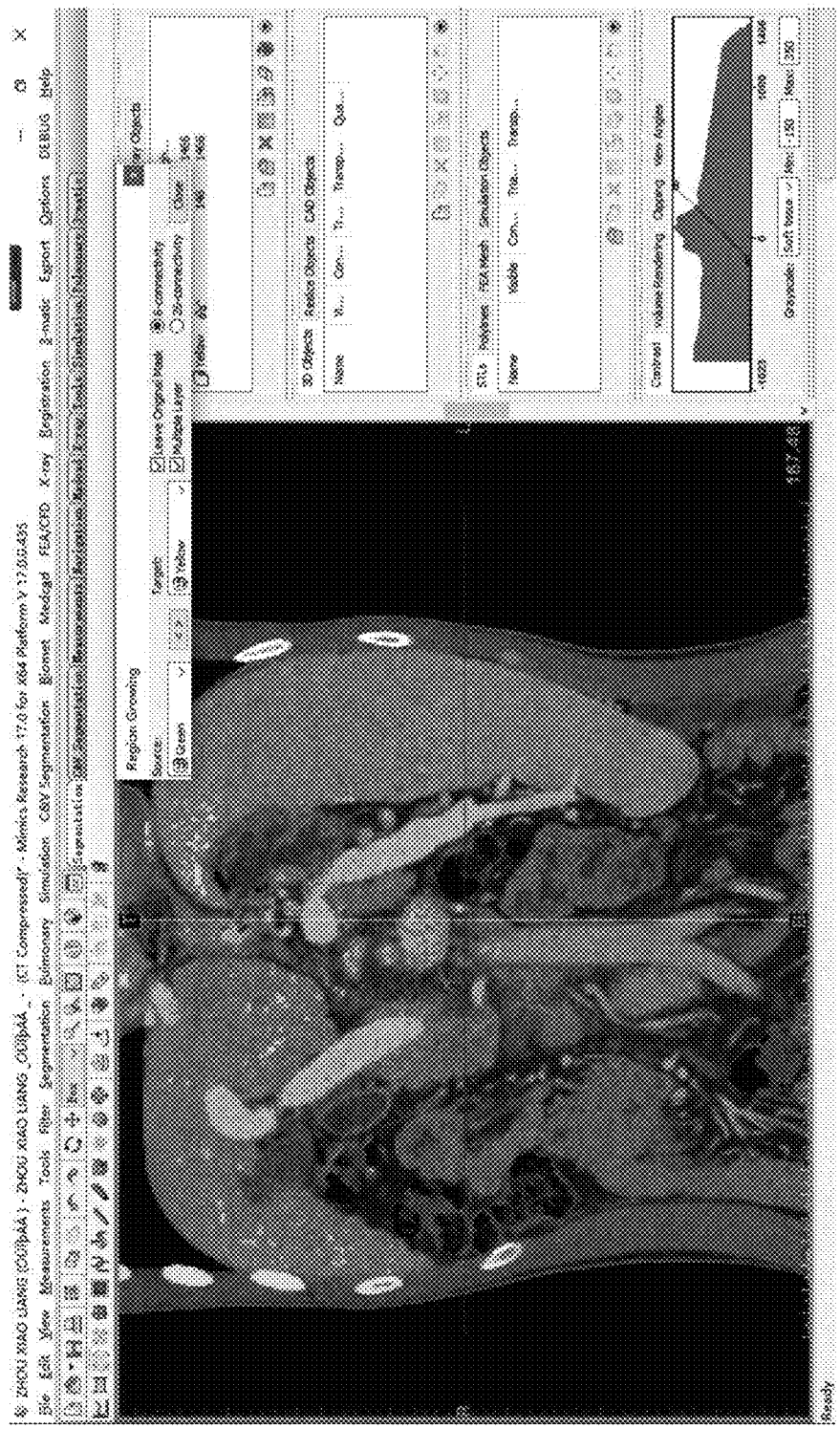
FIG. 7 shows selecting of the area of interest by using Region growing.
Figure 8:
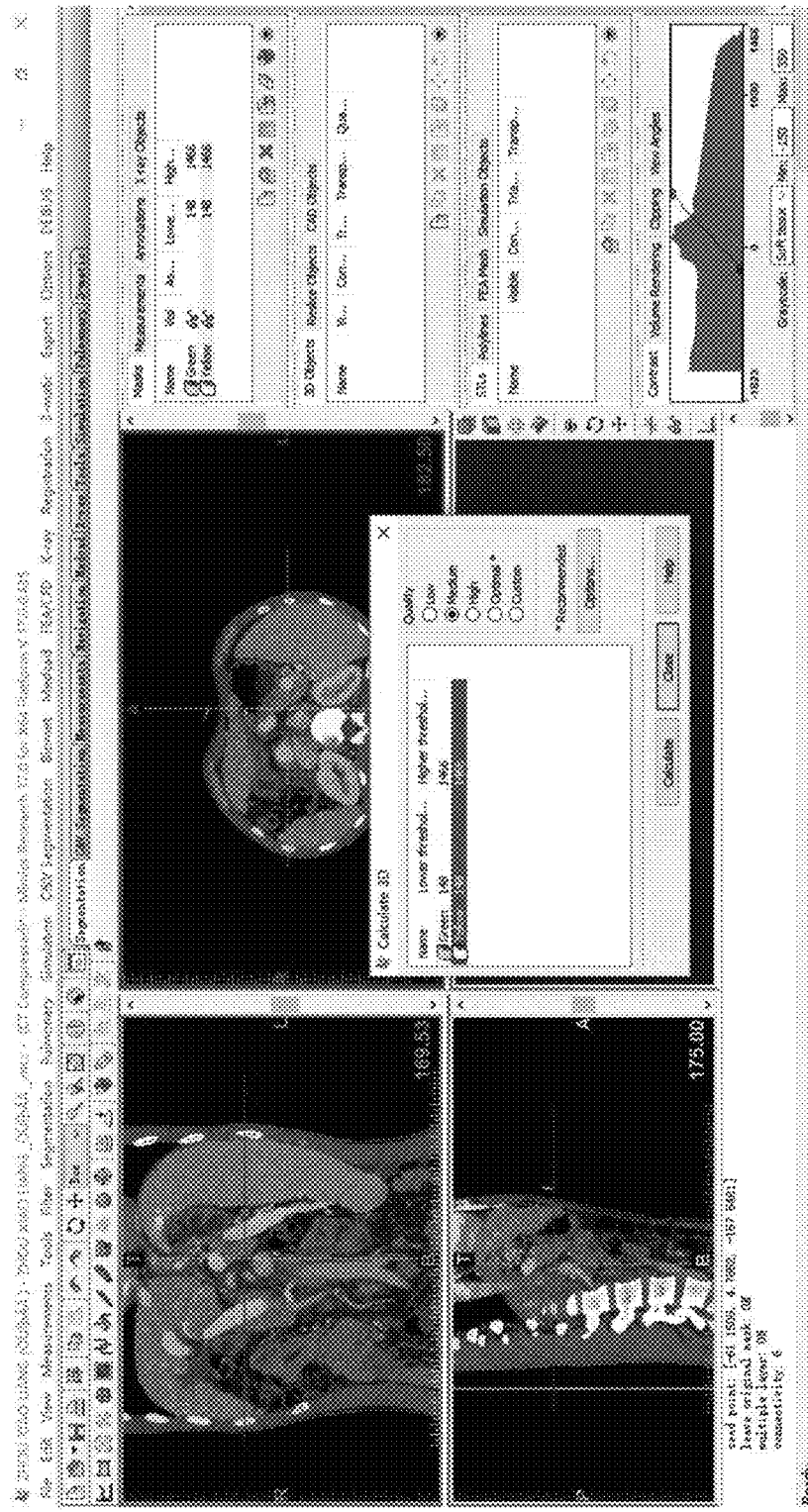
FIG. 8 shows establishing of a preliminary 3D model.
Figure 9:
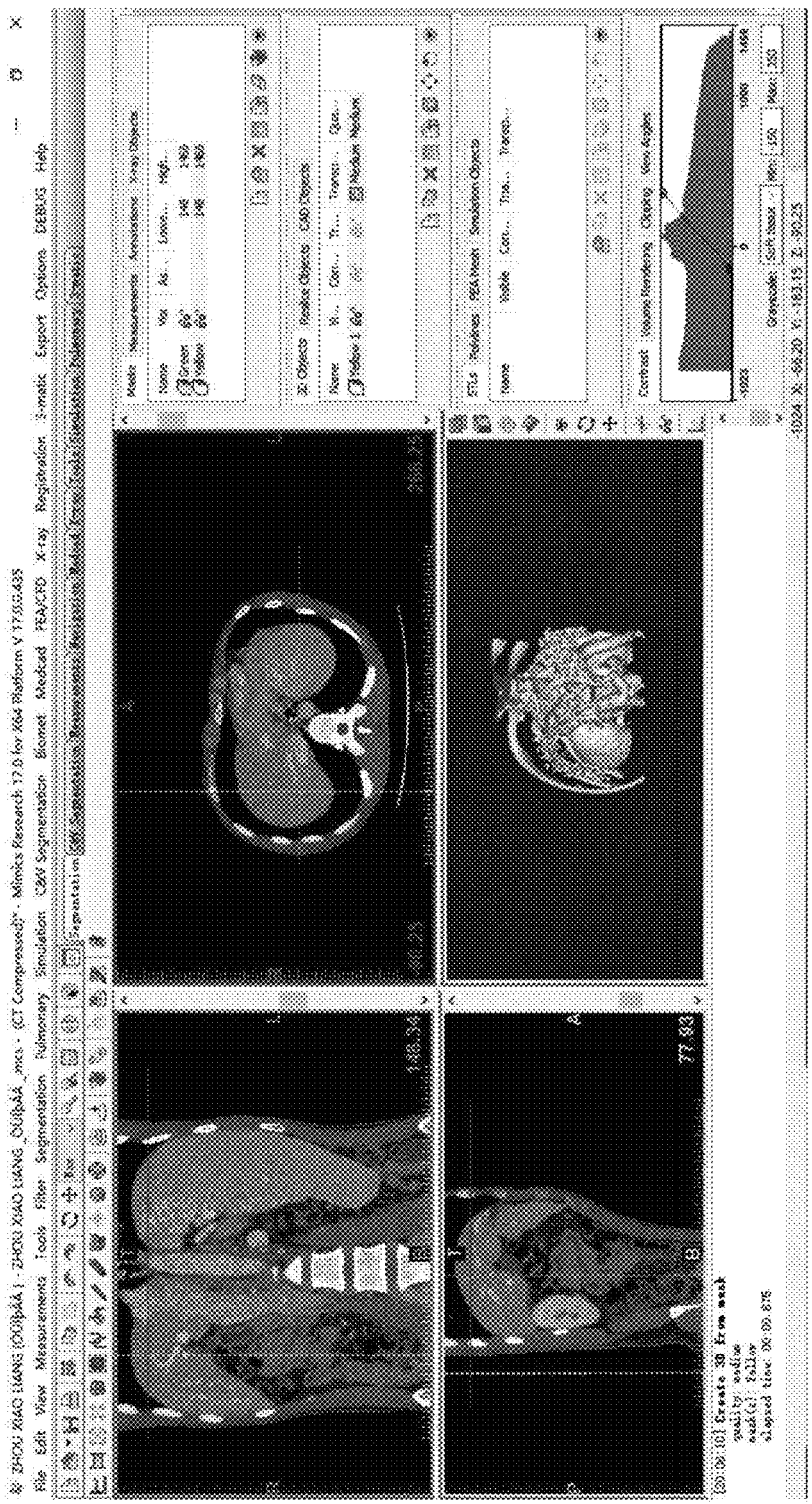
FIG. 9 shows the preliminary 3D model.

3. The hepatic vein-portal vein system (target) is searched in the image, and a threshold range is set by using the Thresholding tool (threshold algorithm based on Hounsfield units) of MIMICS software with the principle of including the CT value of the target and excluding the CT values of the surrounding liver and other soft tissues as much as possible so as to extract the target (FIG. 5); then the masking of the selected hepatic-portal venous region was saved using Crop mask tool (FIG. 6); the target is selected using the Region growing tool of the MIMICS software so as to only extract a structure connected with the target in spatial structure (as shown in FIG. 7); and a preliminary 3D hepatic vein-portal vein model is established by using the Calculate 3D from mask (3D modeling) tool of the MIMICS software and selecting quality to be medium (medium precision) (as shown in FIGS. 8 and 9).

Figure 10:
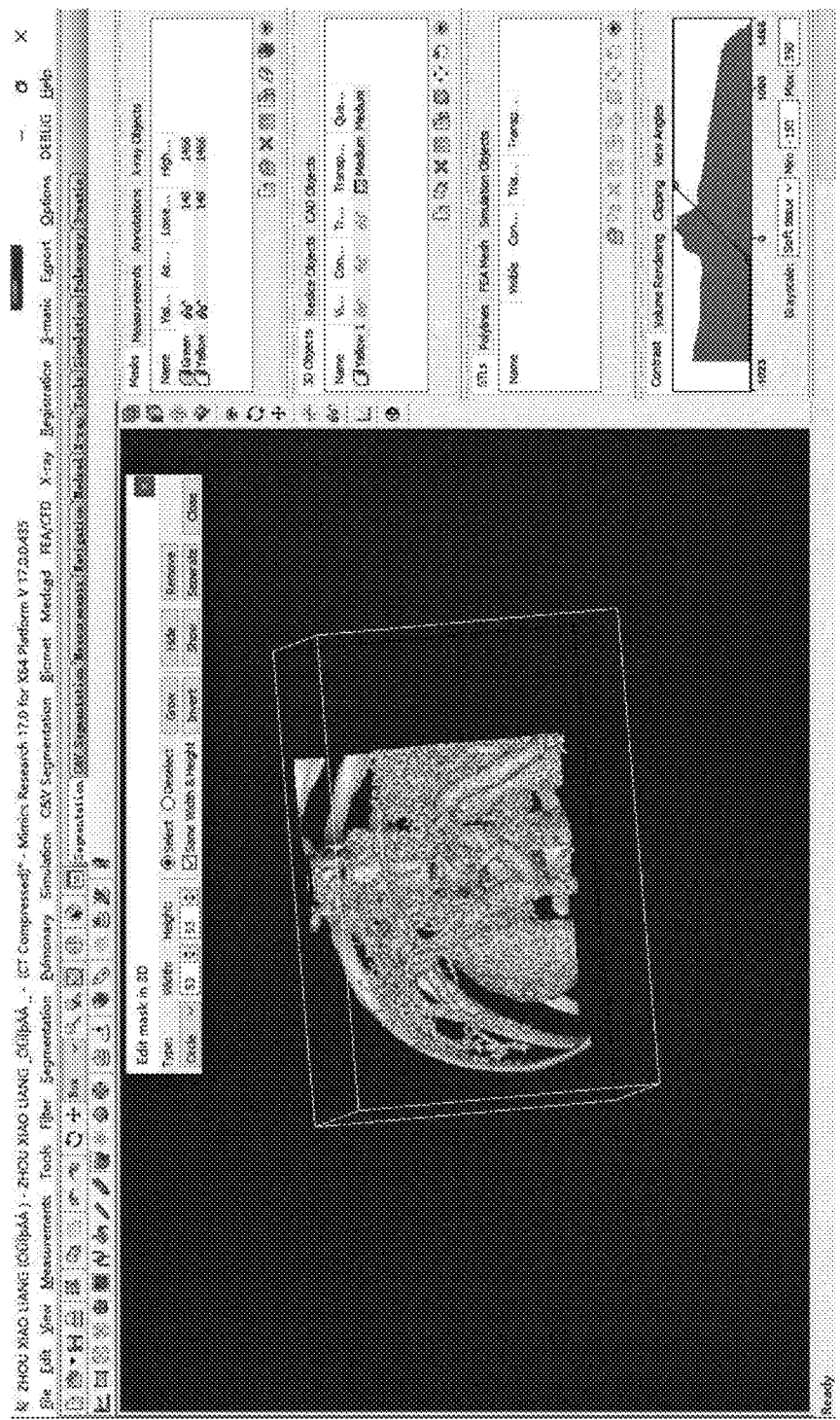
FIG. 10 shows editing of the 3D model by using Edit Masks in 3D.
Figure 11:
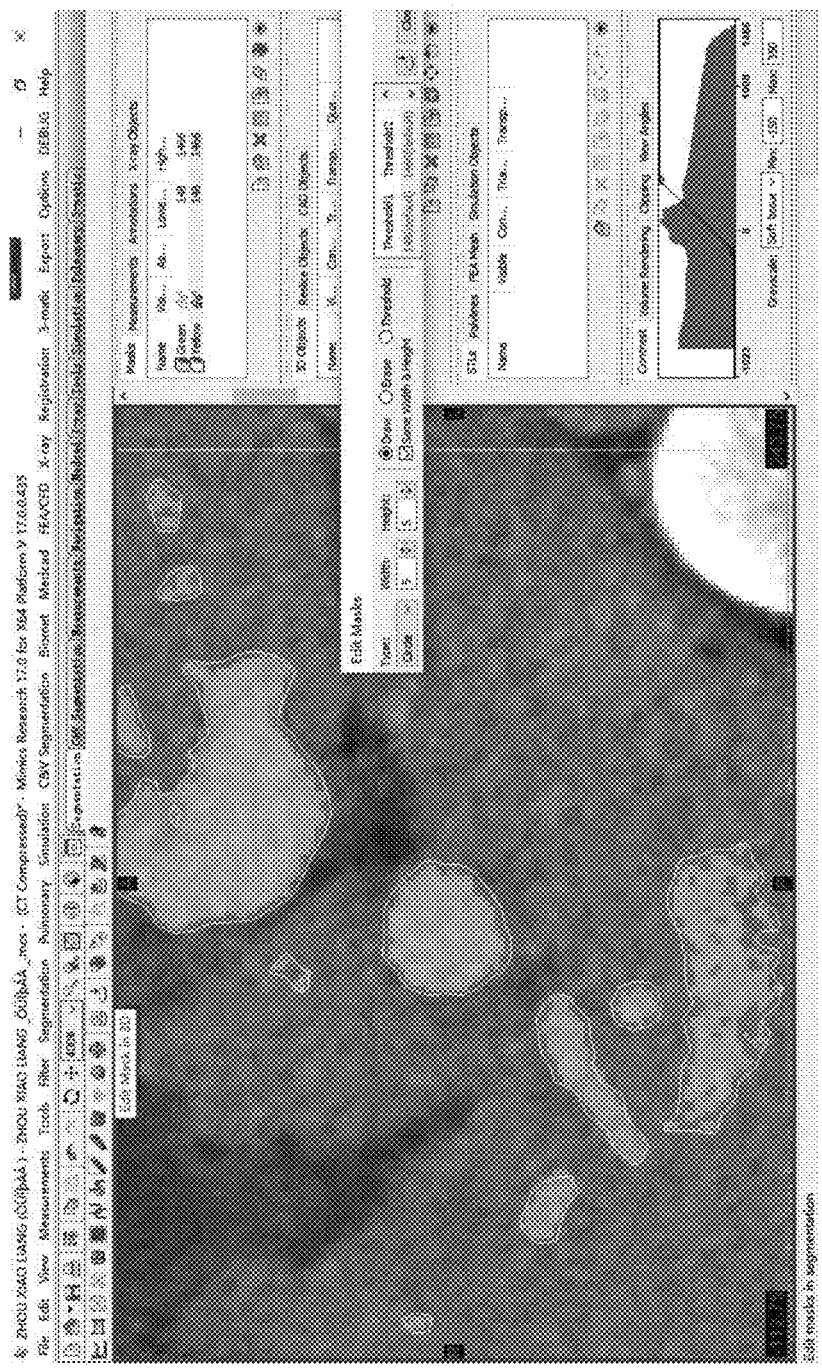
FIG. 11 shows editing of the model by using 2D Edit mask.
Figure 12:
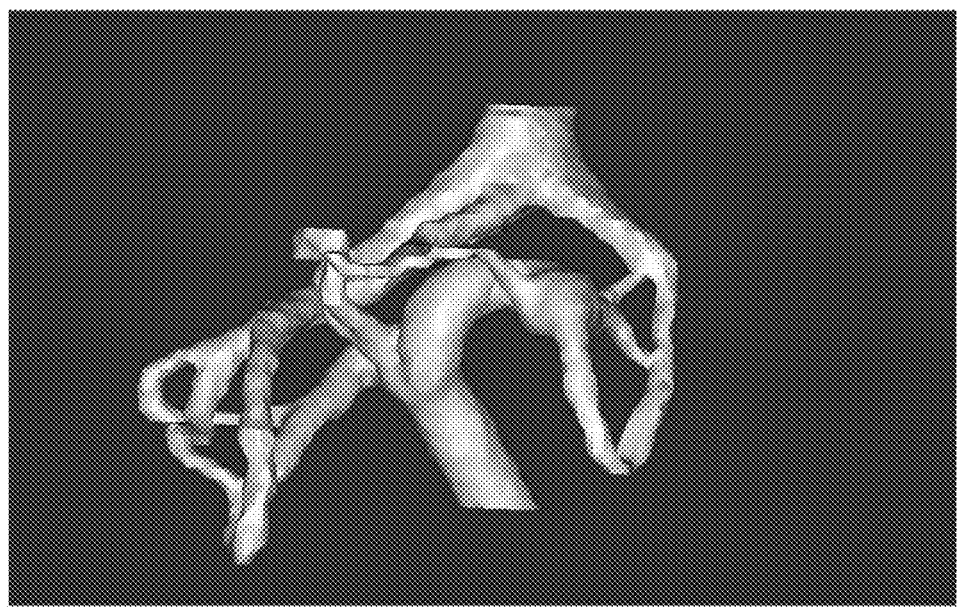
FIG. 12 shows a completely edited model.
Figure 13:
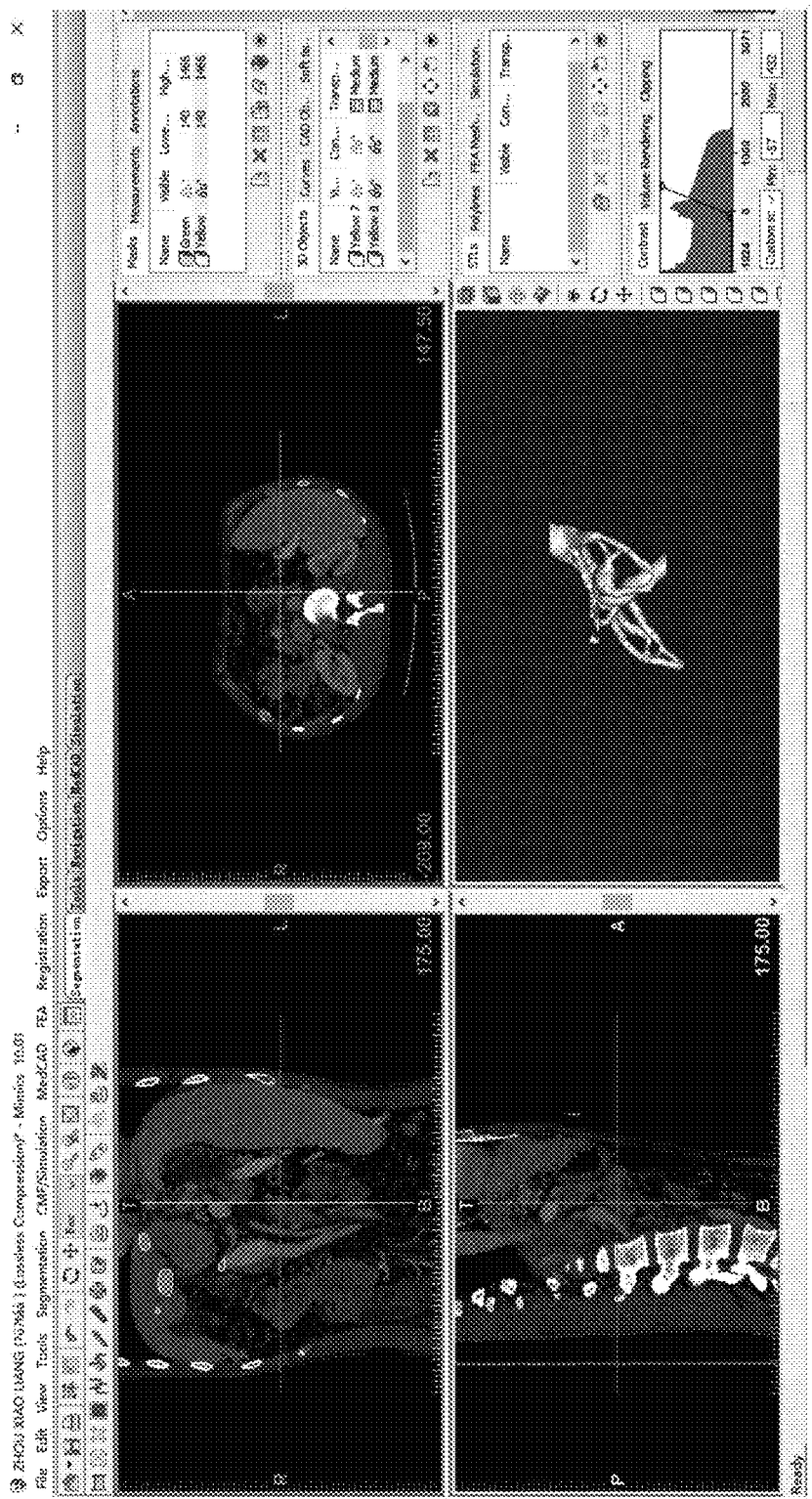
FIG. 13 shows importing the model into mincs 10.01.
Figure 14:
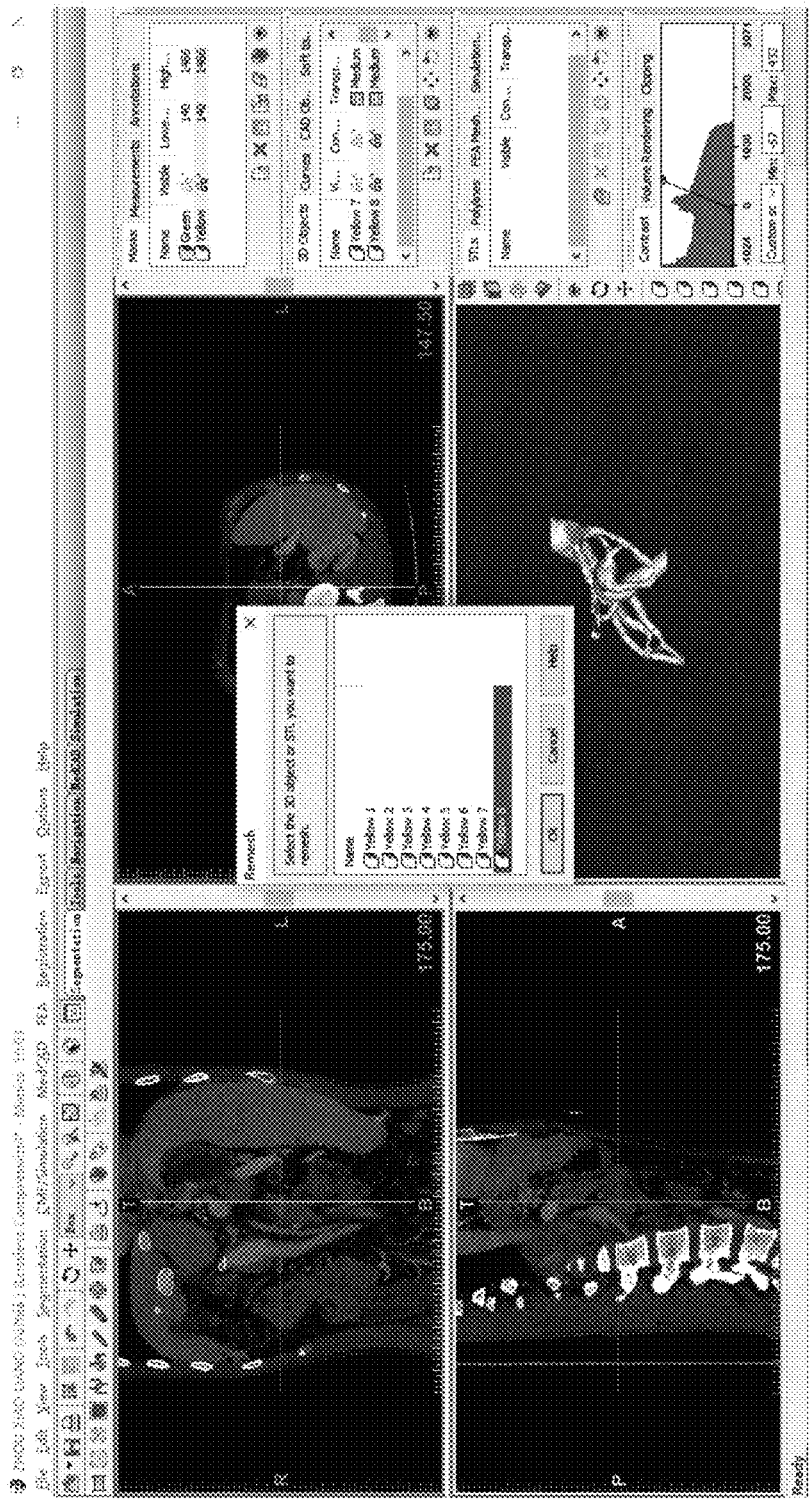
FIG. 14 shows selecting of the completed model and performing of node reducing and Smoothing by using Remesh.
Figure 15:
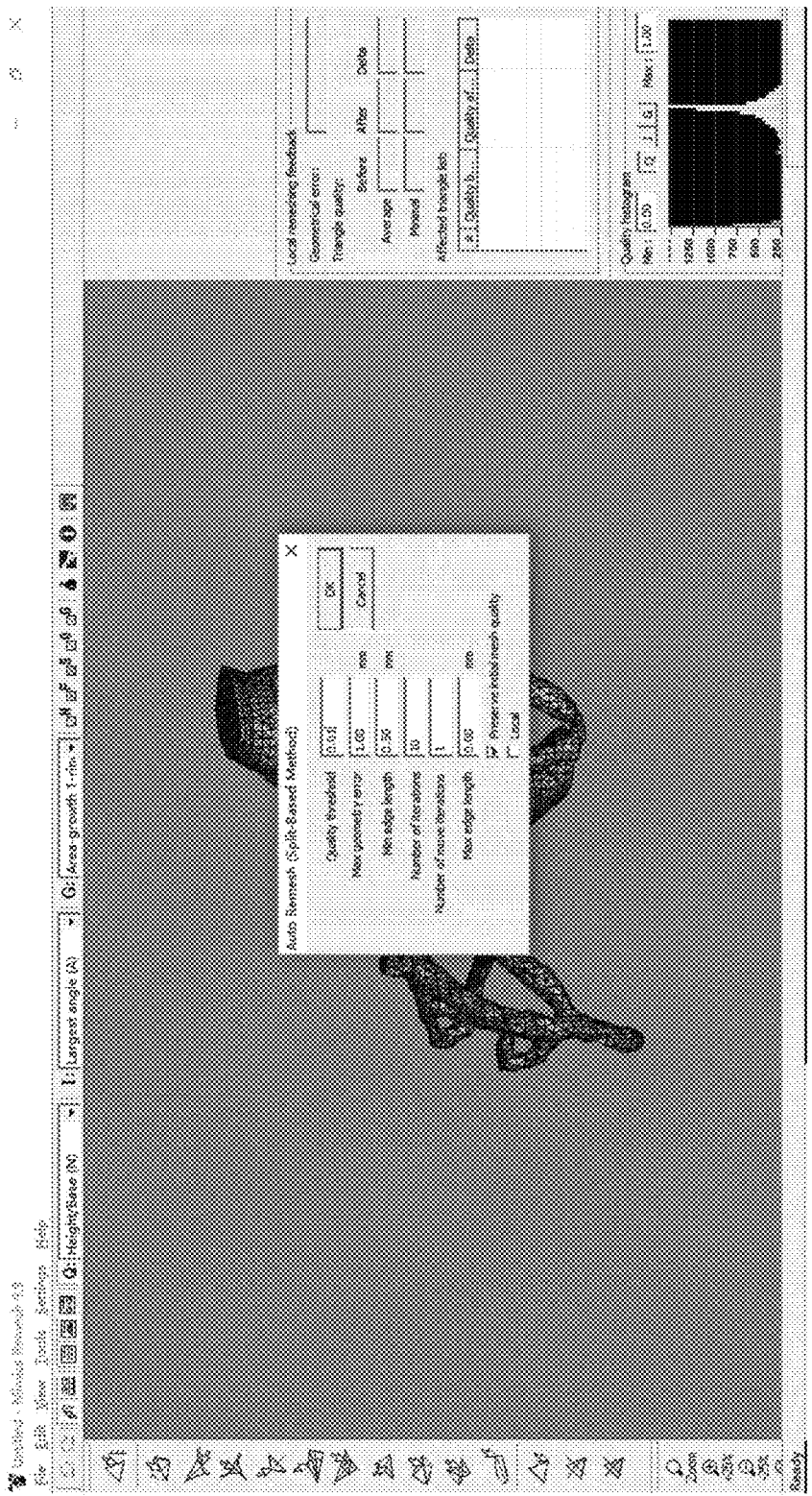
FIG. 15 shows reducing of the node.
Figure 16:
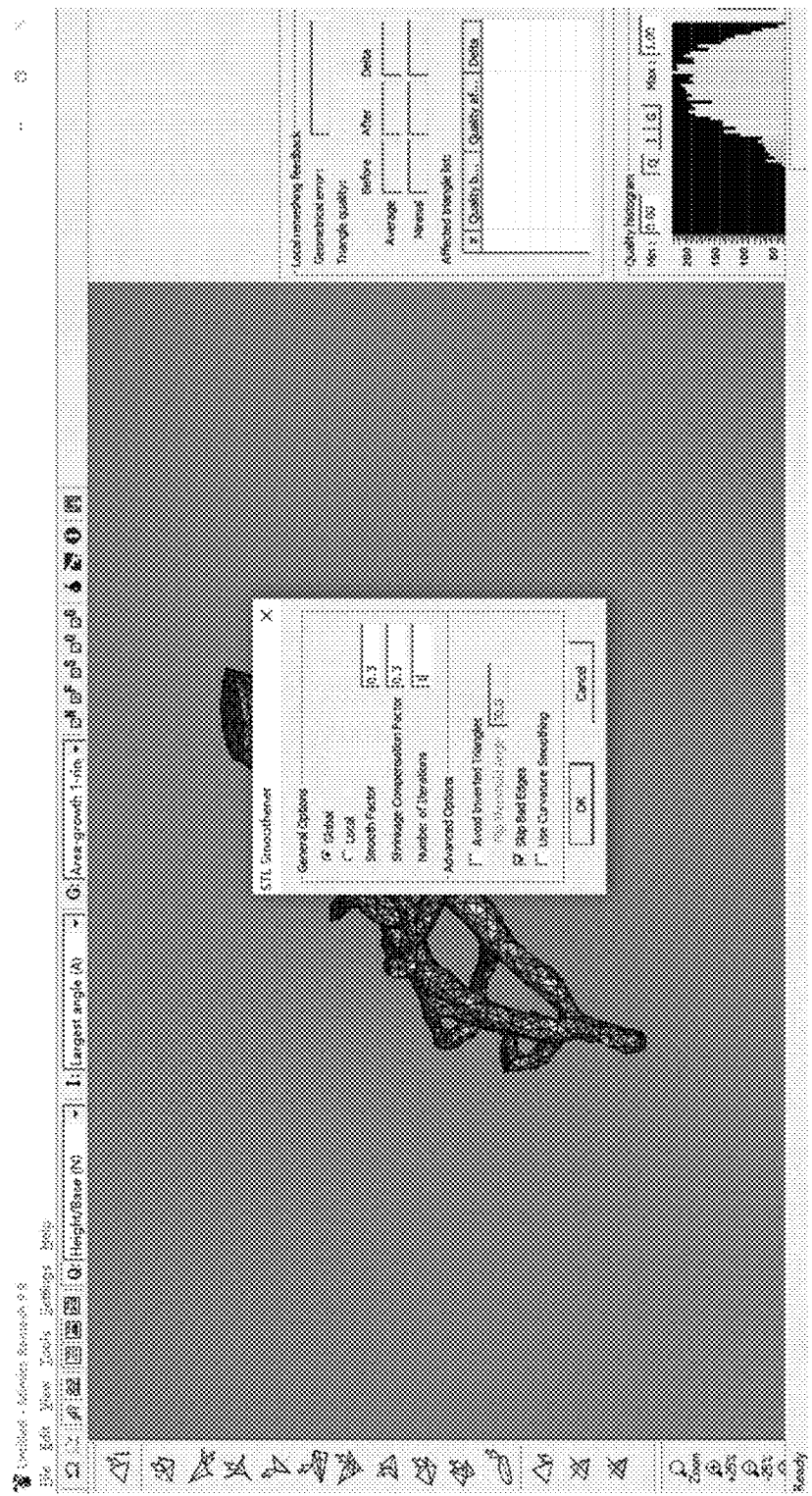
FIG. 16 shows smoothing of the model.
Figure 17:
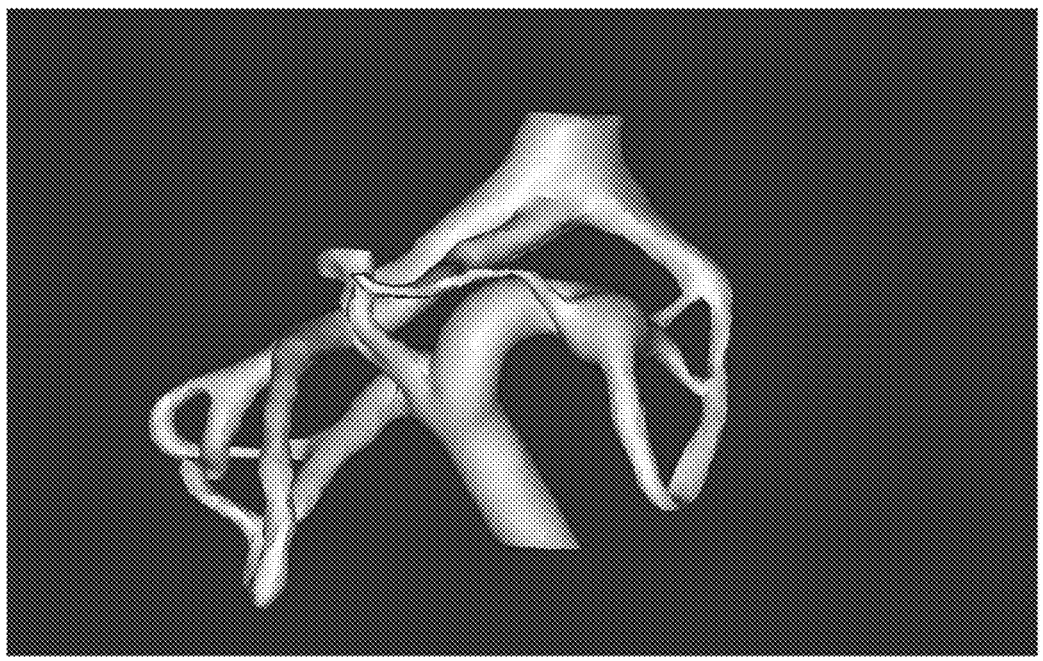
FIG. 17 shows the final smooth model.

4. The residual non-target structures are eliminated and only the hepatic vein-portal vein system is retained using the Edit masks in 3D tool of the MIMICS software (FIG. 10); and the hepatic vein-portal vein system is further selectively filled and noise pixels are eliminated by repeatedly using the Edit masks in 3D (3D cutting) tool and the Edit mask (2D edit mask) tool of the MIMICS software, so as to reconstruct a solid 3D model of hepatic vein-portal vein system with the lumen being closed (FIGS. 11 and 12).

Figure 18:
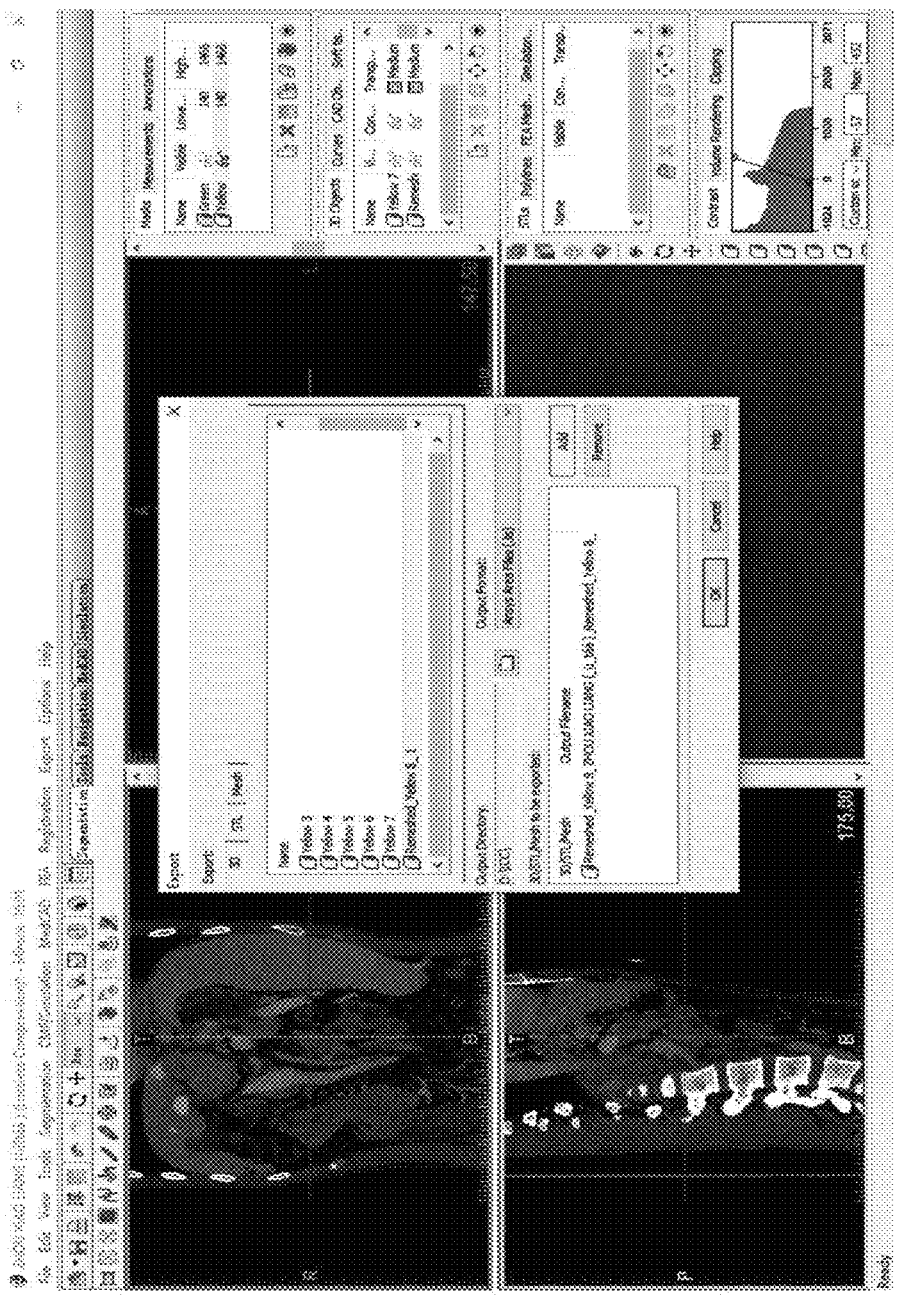
FIG. 18 shows outputting of the files with the format of ansys area file.

5. The remesh technique (split-based method) was applied to remesh the model with the quality-threshold of 0.01; the Smooth tool was used to smoothen the hepatic-portal venous model (FIGS. 13, 14, 15, 16, and 17); then output the model with the format of Ansys area file (.lis) (FIG. 18)

Figure 19:
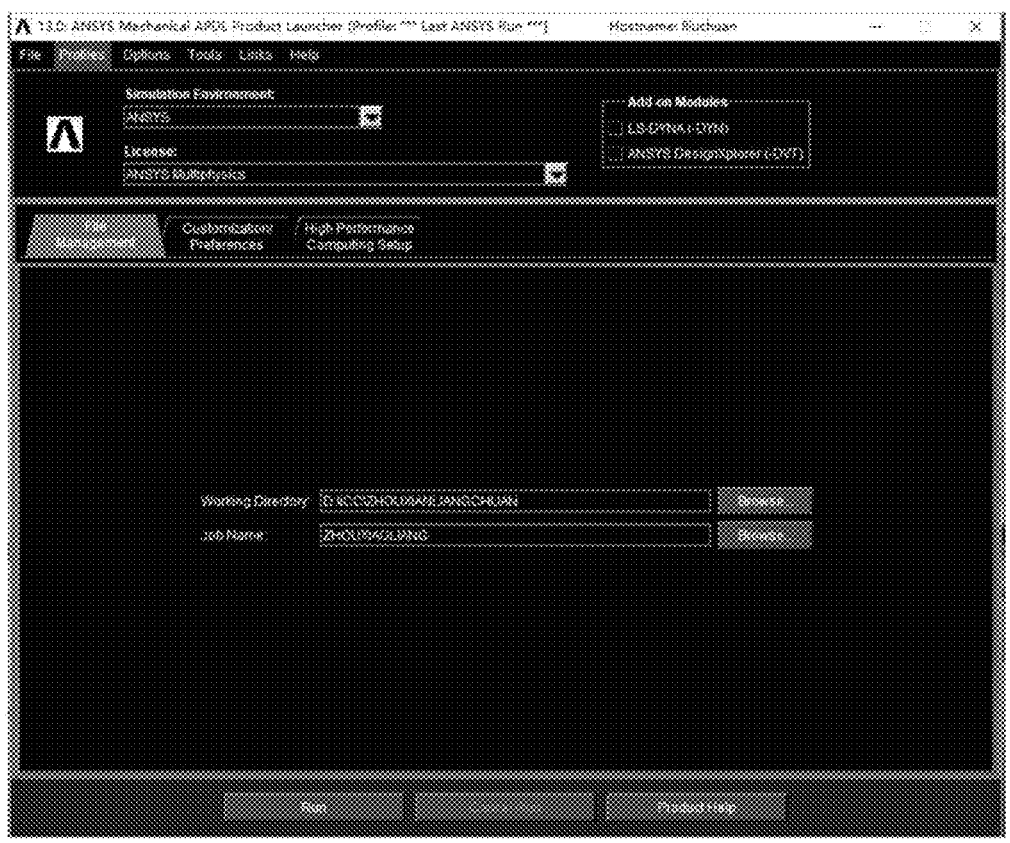
FIG. 19 shows launching the ANSYS classic module from product launcher.
Figure 20:
FIG. 20 shows establishing of a closed volume model on the basis of area.

6. The area element (with the format .lis) was imported in the classic mode of ANSYS (FIG. 19), and the unit of length was unified as the international unit m; and a solid model of hepatic vein-portal vein system model was established on the basis of area (FIG. 20).

Figure 21:
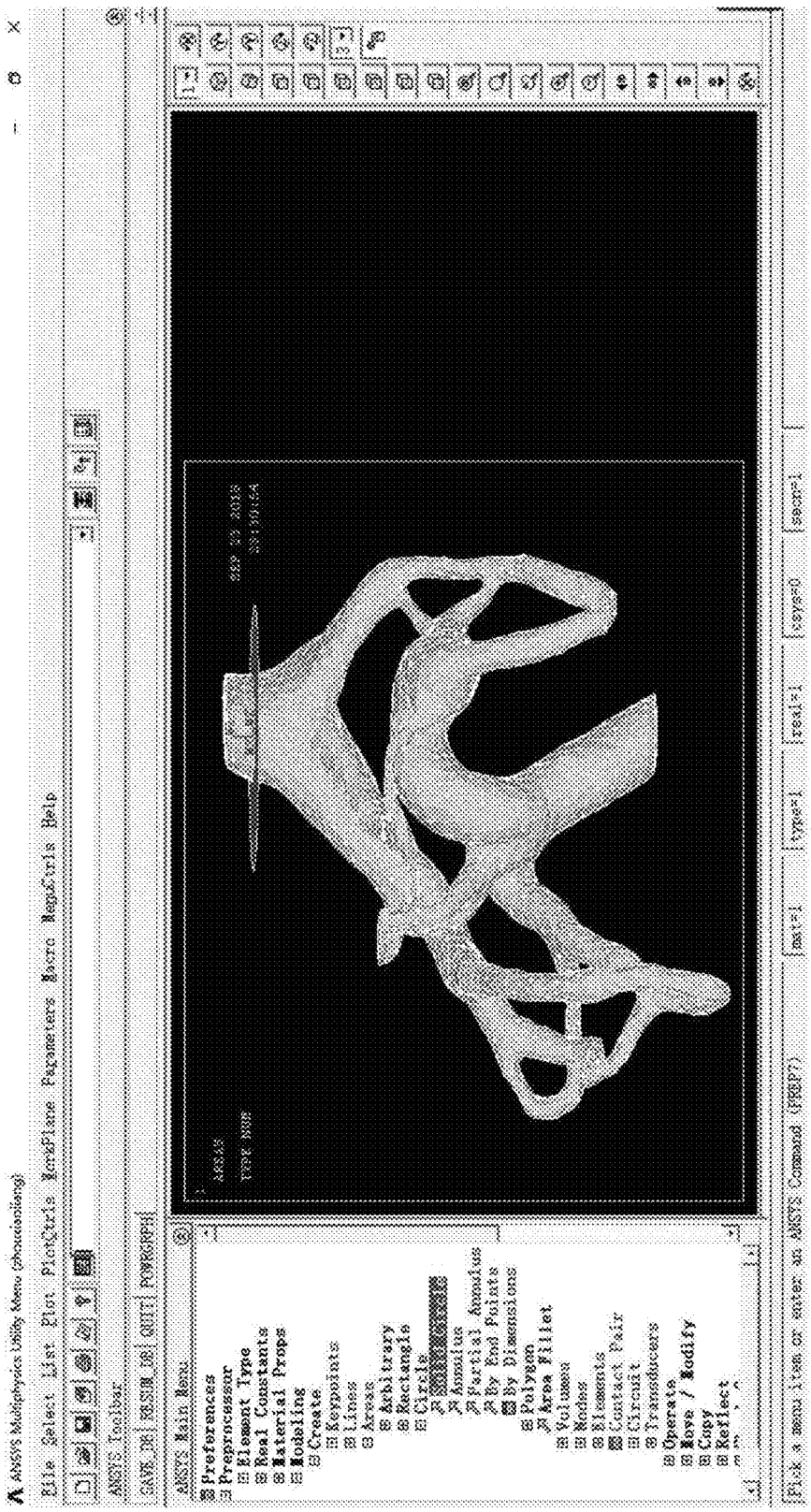
FIG. 21 shows making a section of blood inlet.
Figure 22:
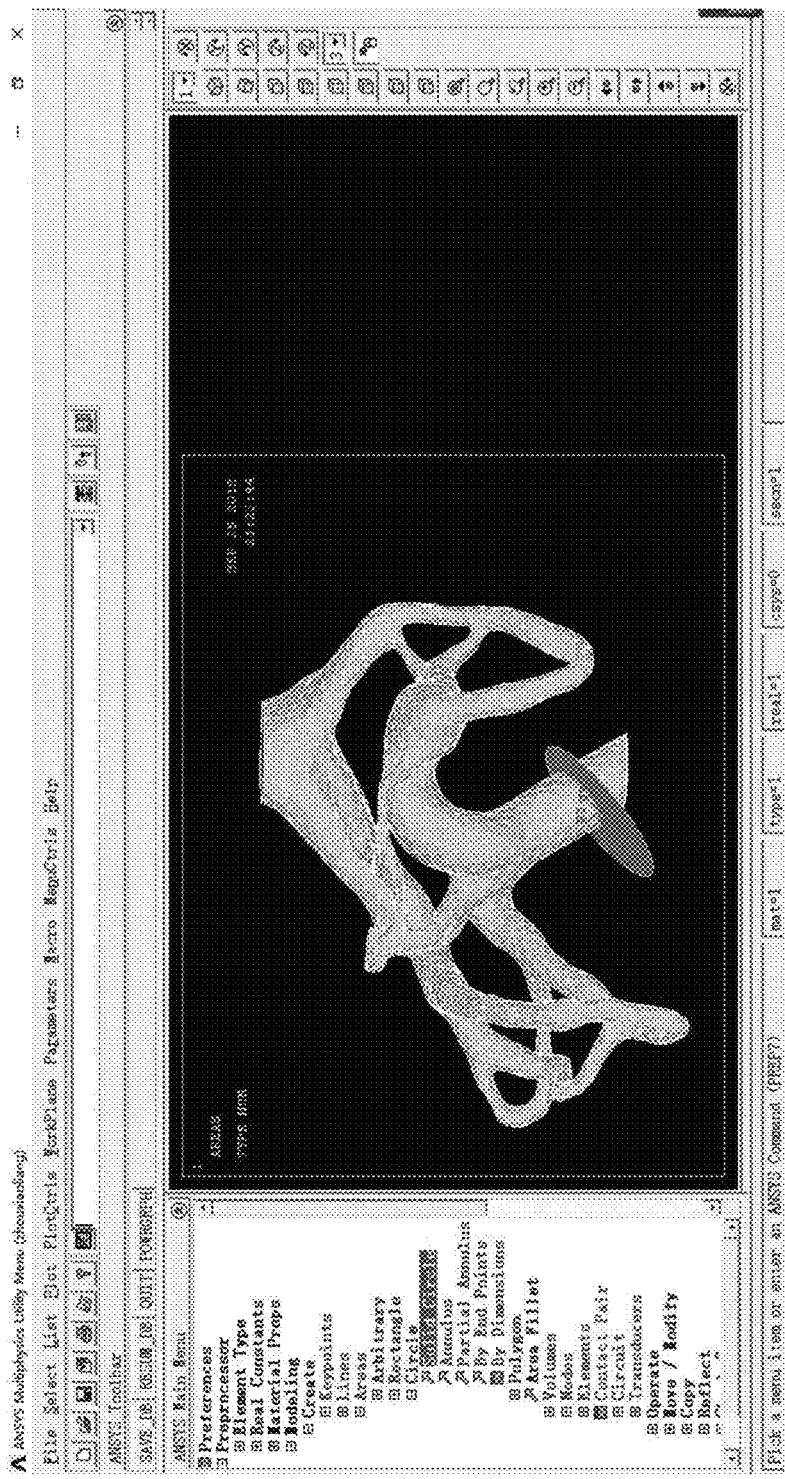
FIG. 22 shows making a section of blood outlet.
Figure 23:
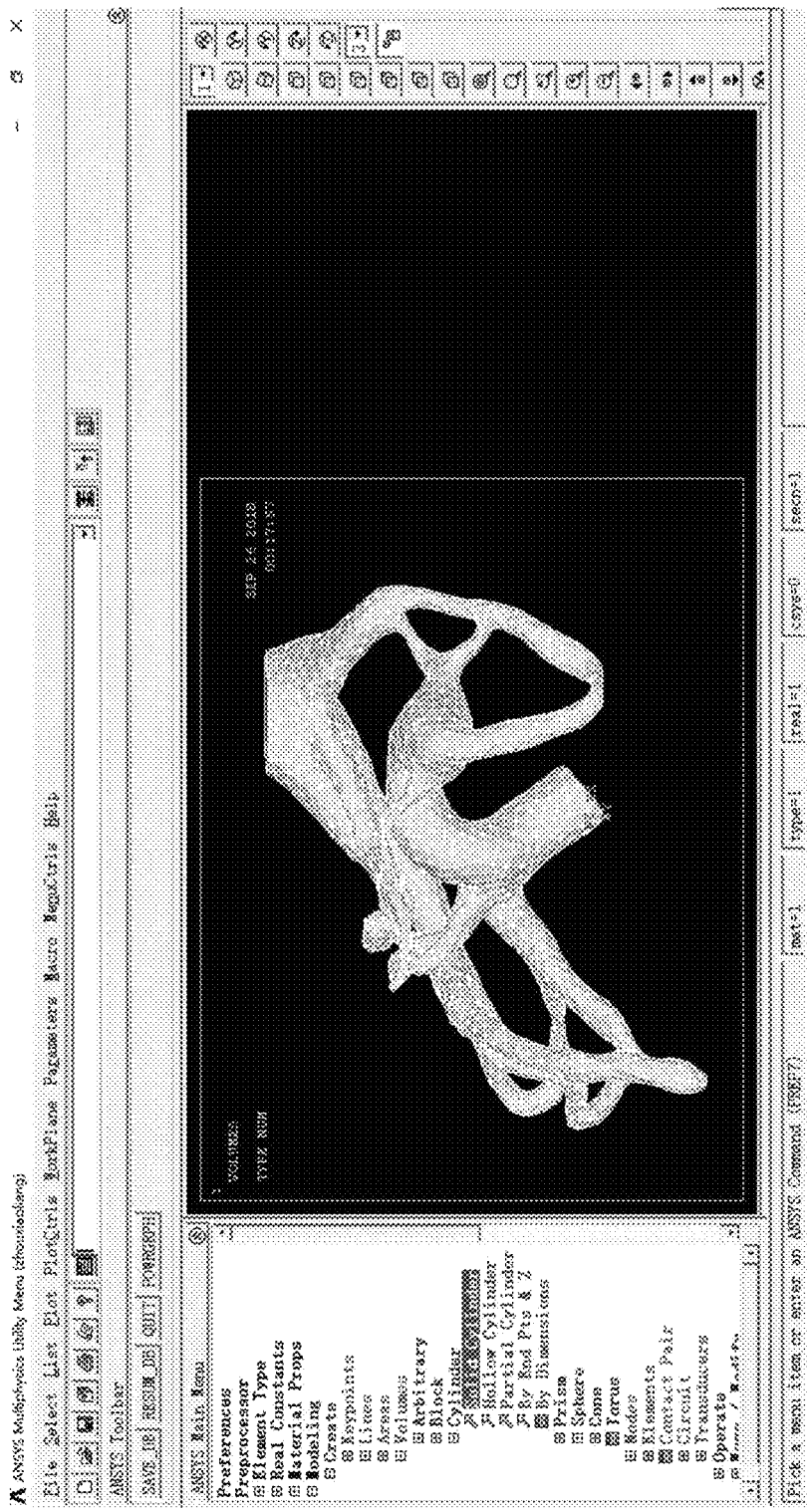
FIG. 23 shows a finished vFHVP model.

7. A vertical section of the blood inlet and outlet of the hepatic vein-portal vein system model is made by Boolean operation, to obtain an open geometric model of the virtual free hepatic venous pressure (vFHVP) (as shown in FIGS. 21, 22 and 23); and thereafter the file is exported with the suffix .IGS for use (IGS is a file format of 3D numerical model, which is readable by the ANSYS Workbench module).

Figure 24:
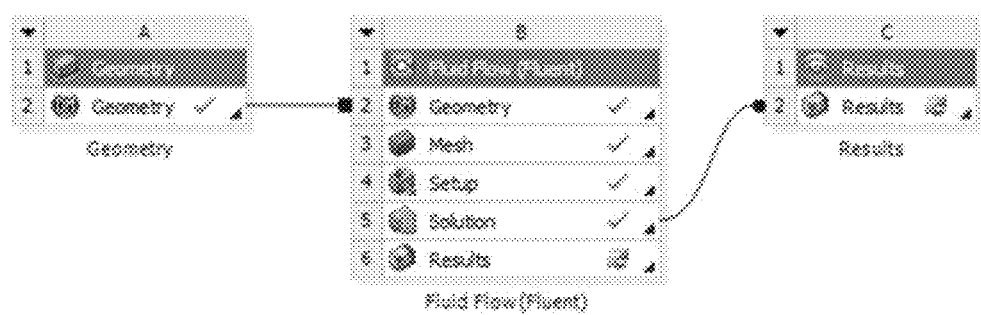
FIG. 24 shows the ANSYS Workbench finite element analysis calculation platform.
Figure 25:
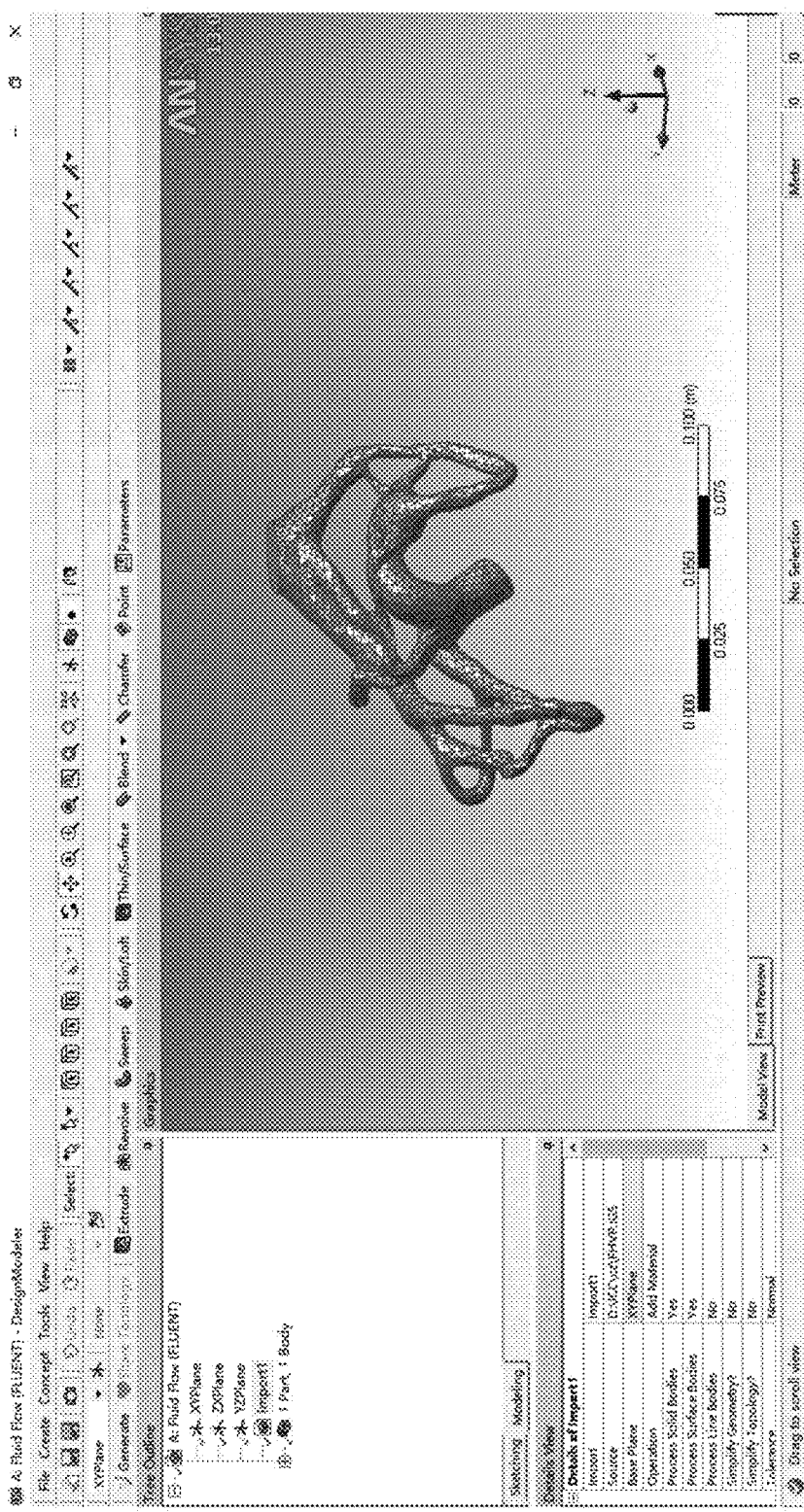
FIG. 25 shows a geometrical model in ansys fluent.
Figure 26:
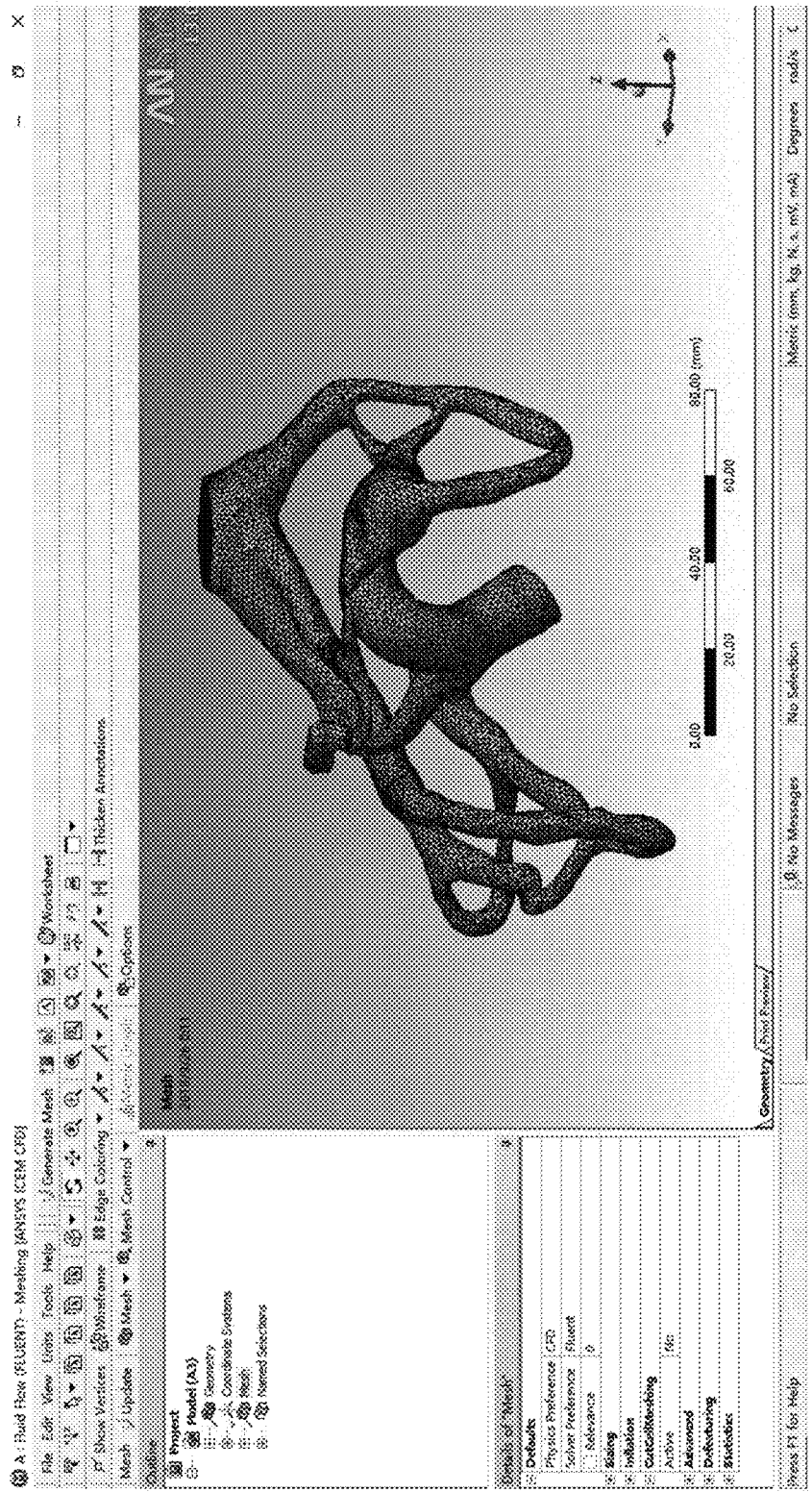
FIG. 26 shows meshing of the geometric model into finite elements.

8. An ANSYS Workbench finite element calculation platform is established (as shown in FIG. 24), including a geometrical model module Geometry, a fluid calculation module Fluent and a Results module (i.e., CFD-POST post-processing module), the IGS file is imported through the Geometry module, in a Mesh unit, the objects of meshing are imported numerical models and the meshing method is set as Tetrahedrons; CFD (Computational Fluid Dynamics) is selected in Physics Preference, and Fluent is selected in Solver Preference (solving the flow field using Fluent); the mesh size is defined in consideration of the operation accuracy and the computer running speed, the max face size is set to 1.5 mm and the max size is set to 4 mm; and thereafter meshing is accomplished through Generate Mesh (FIGS. 25 and 26).

Figure 27:
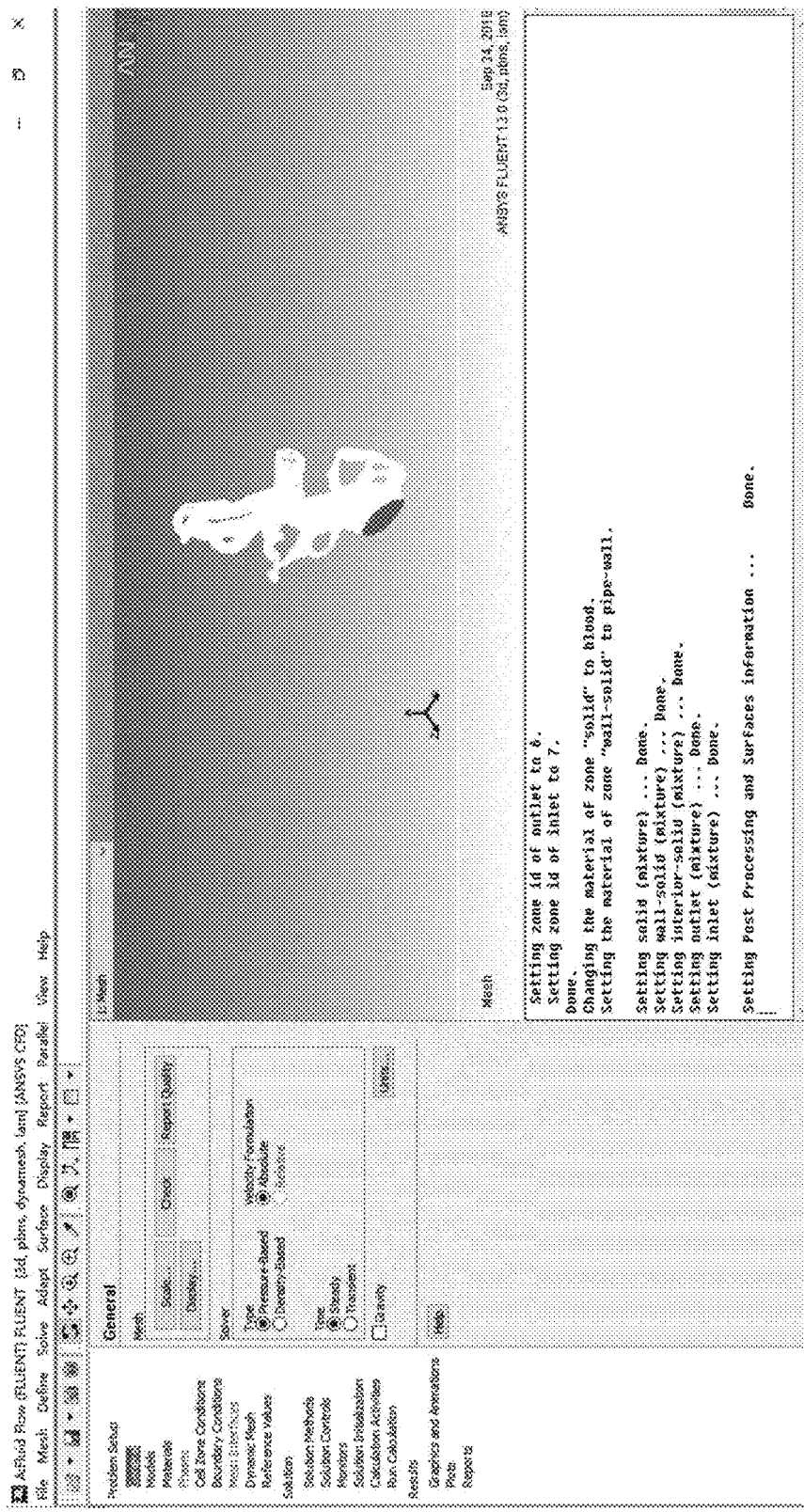
FIG. 27 shows entering into the CFD.
Figure 28:
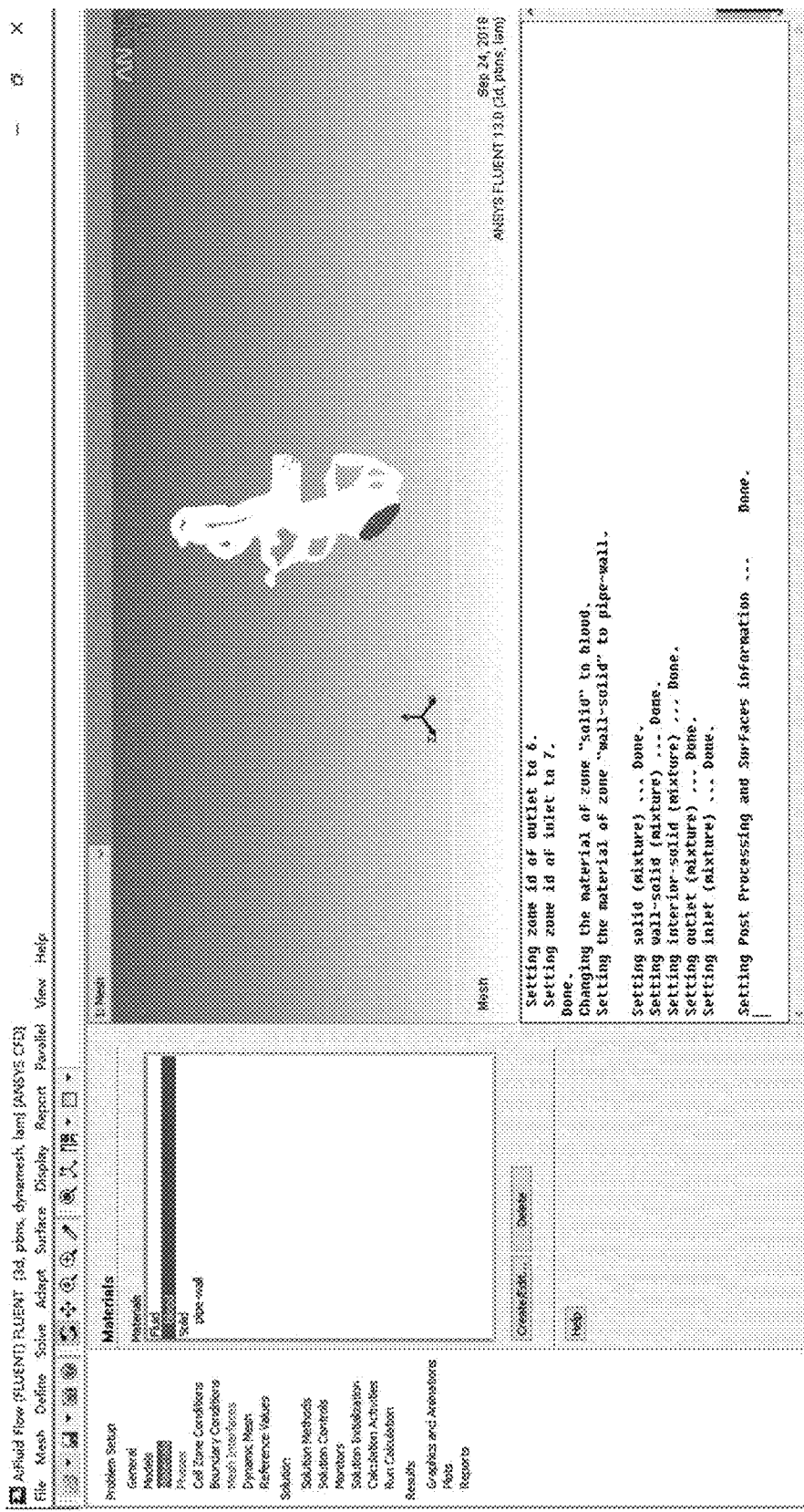
FIG. 28 shows setting of the blood parameters.
Figure 29:
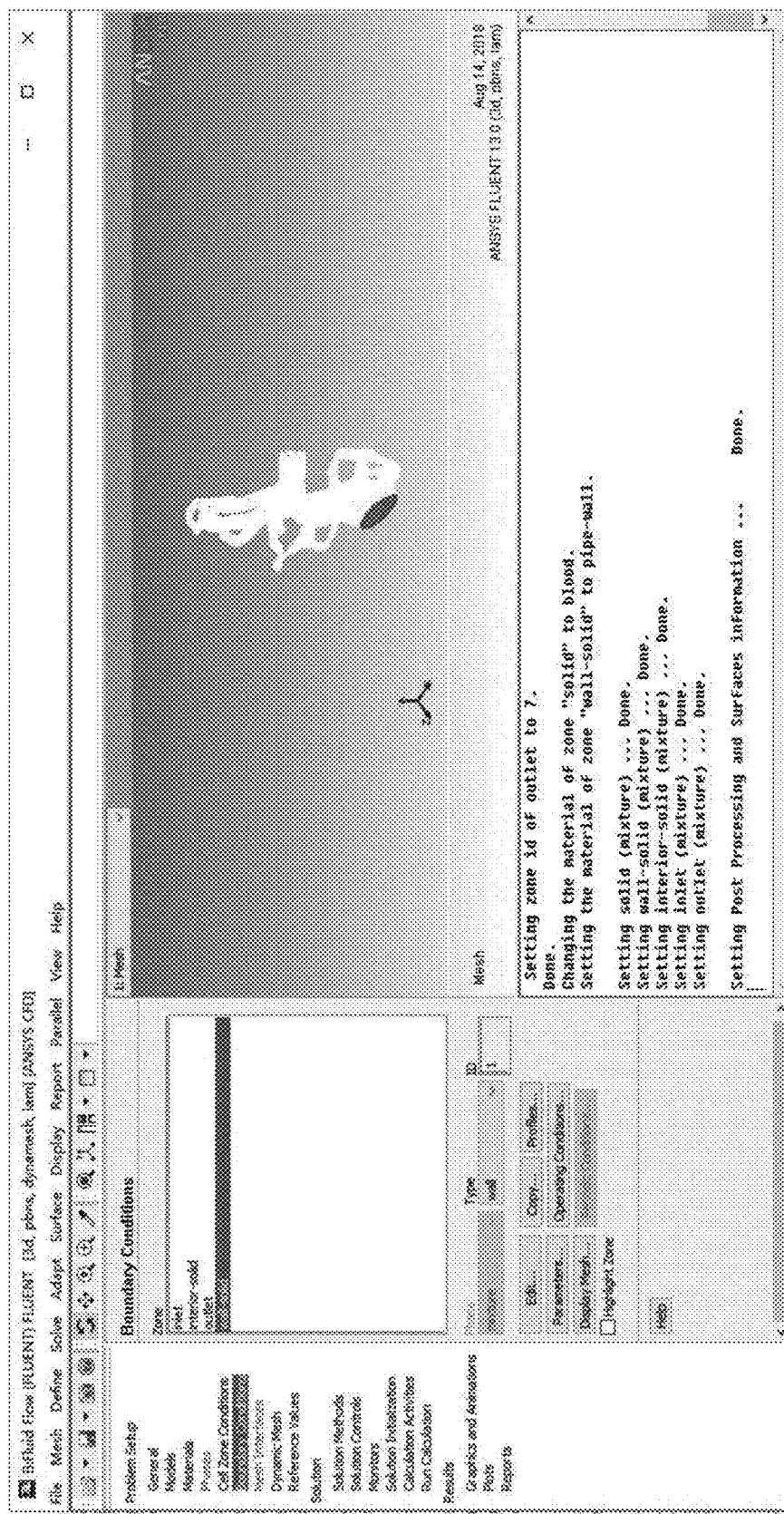
FIG. 29 shows the boundary conditions.
Figure 30:
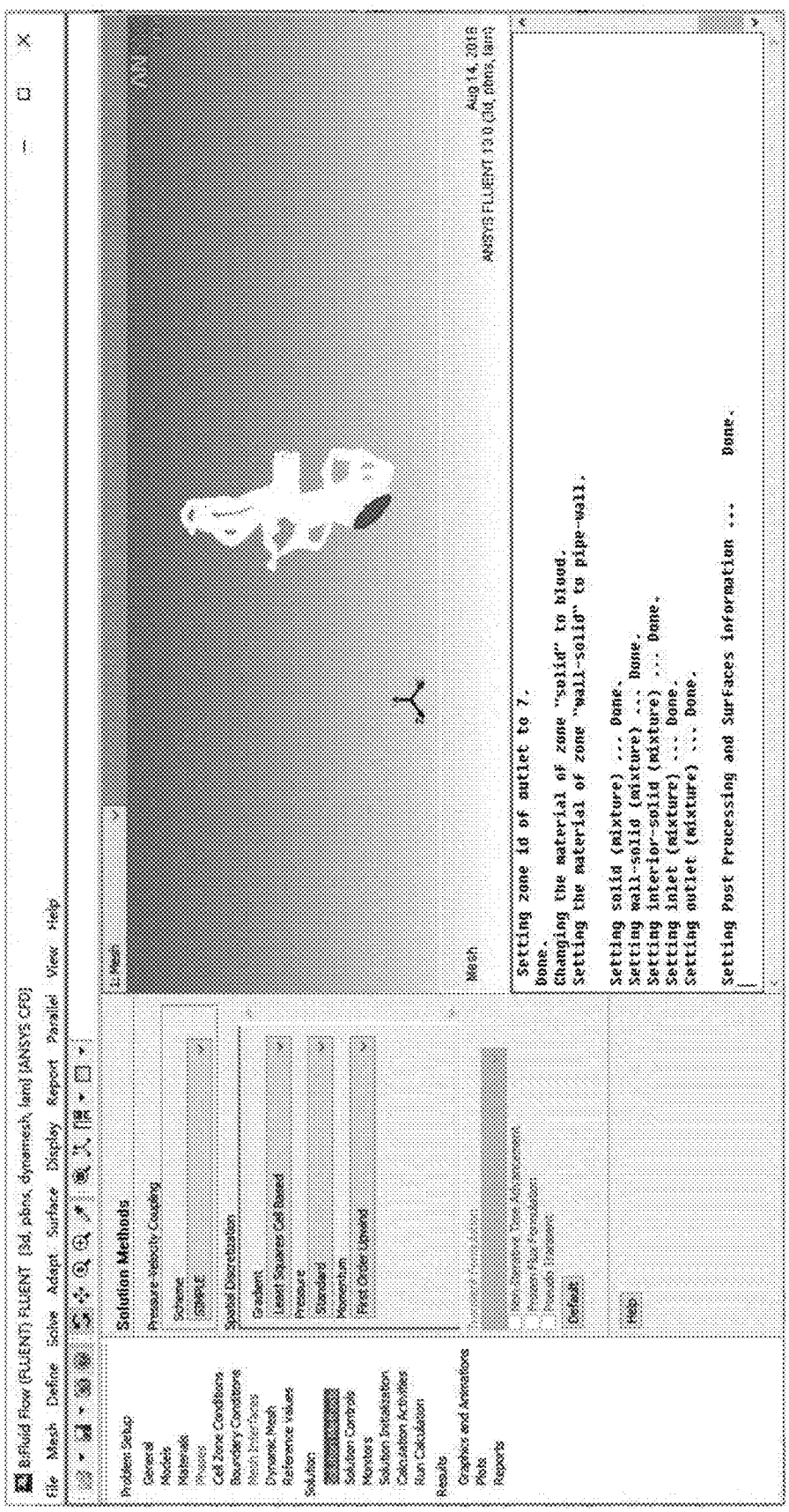
FIG. 30 shows setting of the algorism.
Figure 31:
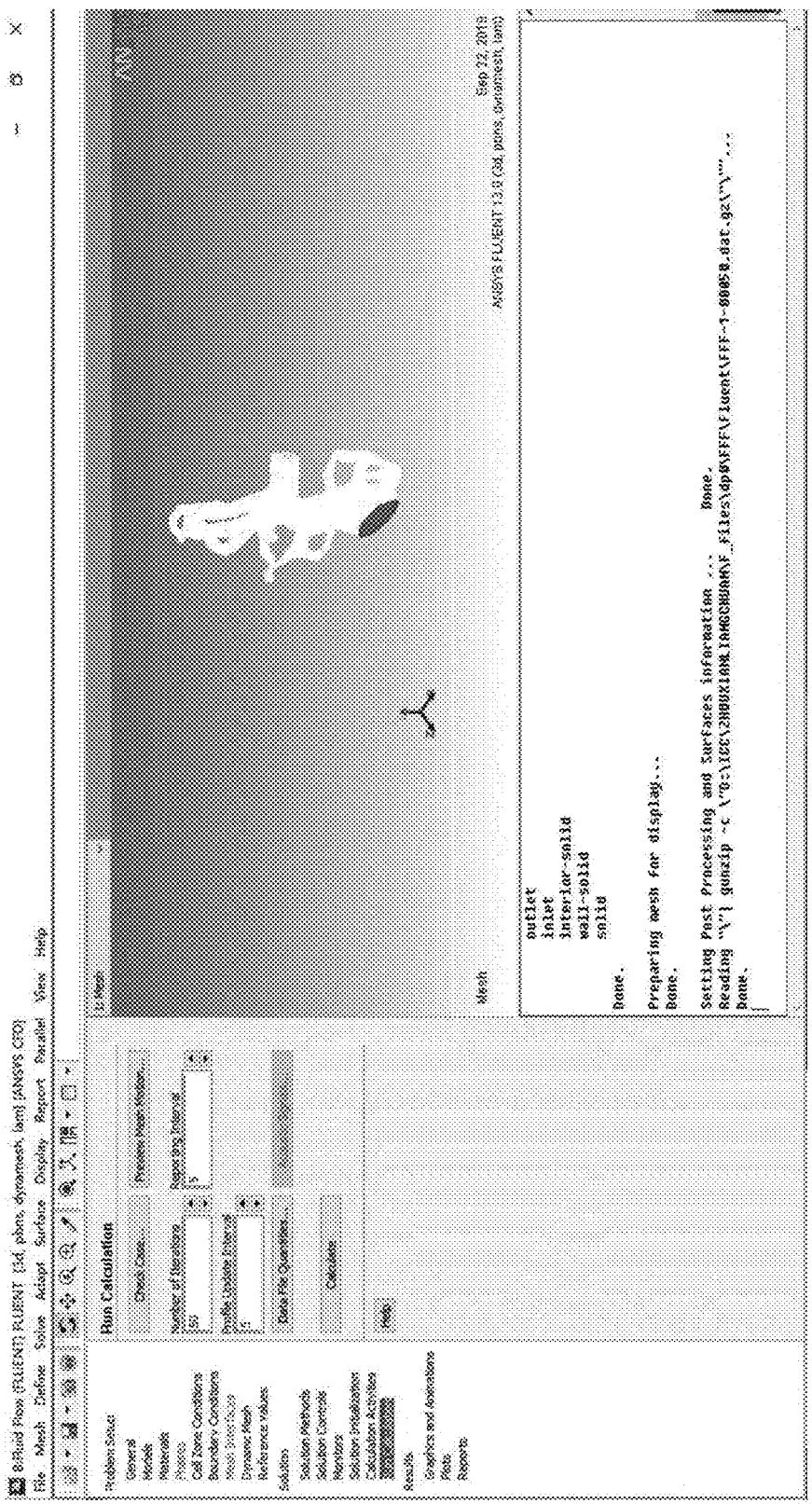
FIG. 31 shows setting and calculating of the number of iterations.

9. Material parameters (blood density, blood viscosity, blood vessel wall density) are set in solution of the fluid dynamics calculation module Fluent to make the physical properties of the model close to the biological properties of human body so as to improve the accuracy of simulation (FIG. 27); control parameters (calculating the step size, the number of iterations, the maximum number of cycles) and boundary conditions are solved (naming the blood inlet surface and providing therefor a velocity value, naming the outlet surface and then providing therefor a pressure value, and setting an unnamed blood vessel wall as wall), the Reynolds number of portal vein flow is $R\varepsilon<2000$, so the simulation fluid is set as a laminar flow; the operation initialization is set to start from the inlet surface; and the fluid-solid coupling between the blood vessel wall and the blood is simulated after the completion of the parameter setting described above, and the pressure distribution and blood flow distribution of the simulation 3D blood vessel model are obtained by calculation (FIGS. 28, 29, 30 and 31).

Figure 32:
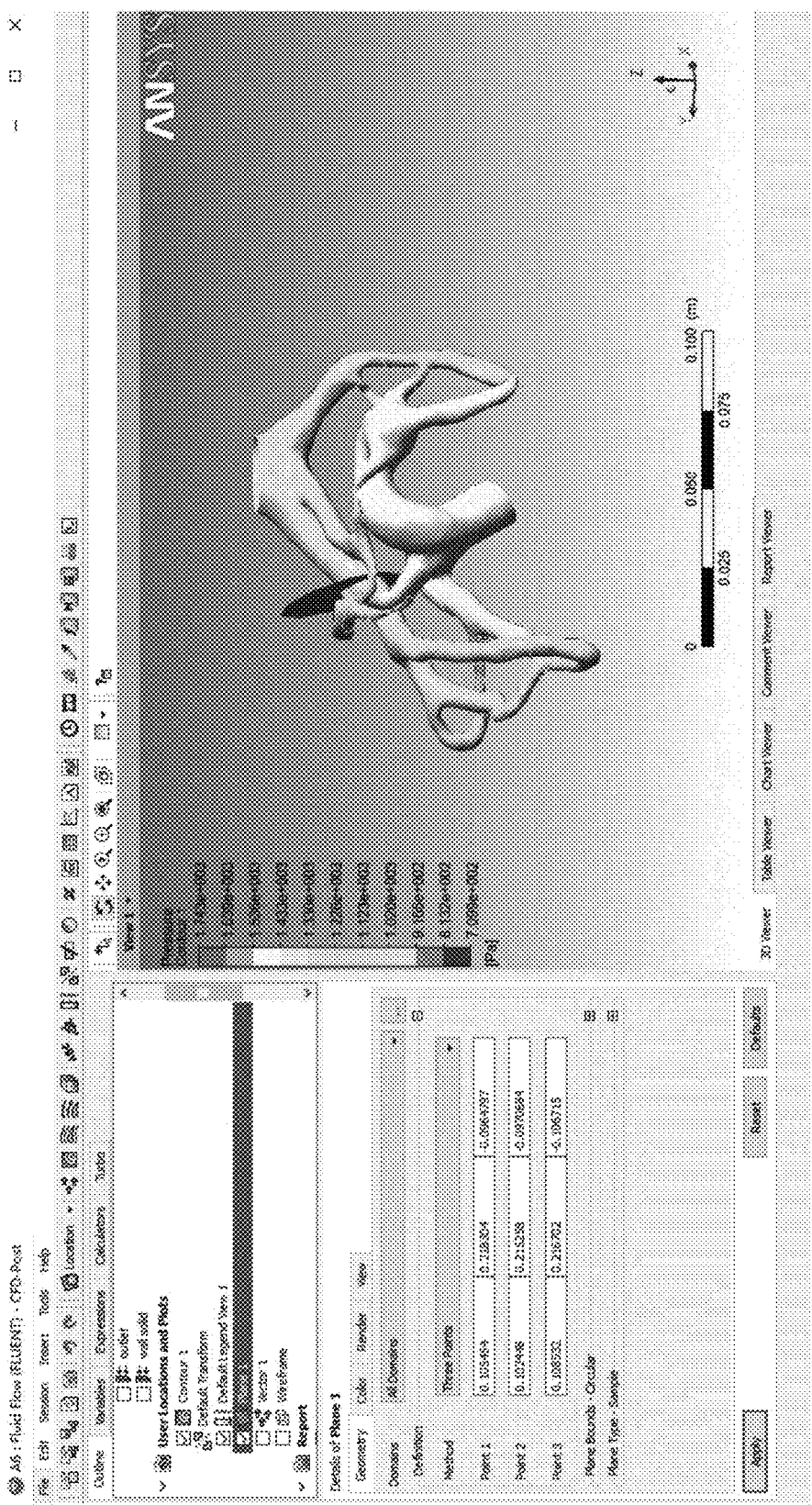
FIG. 32 shows setting of the panel to read vFHVP.
Figure 33:
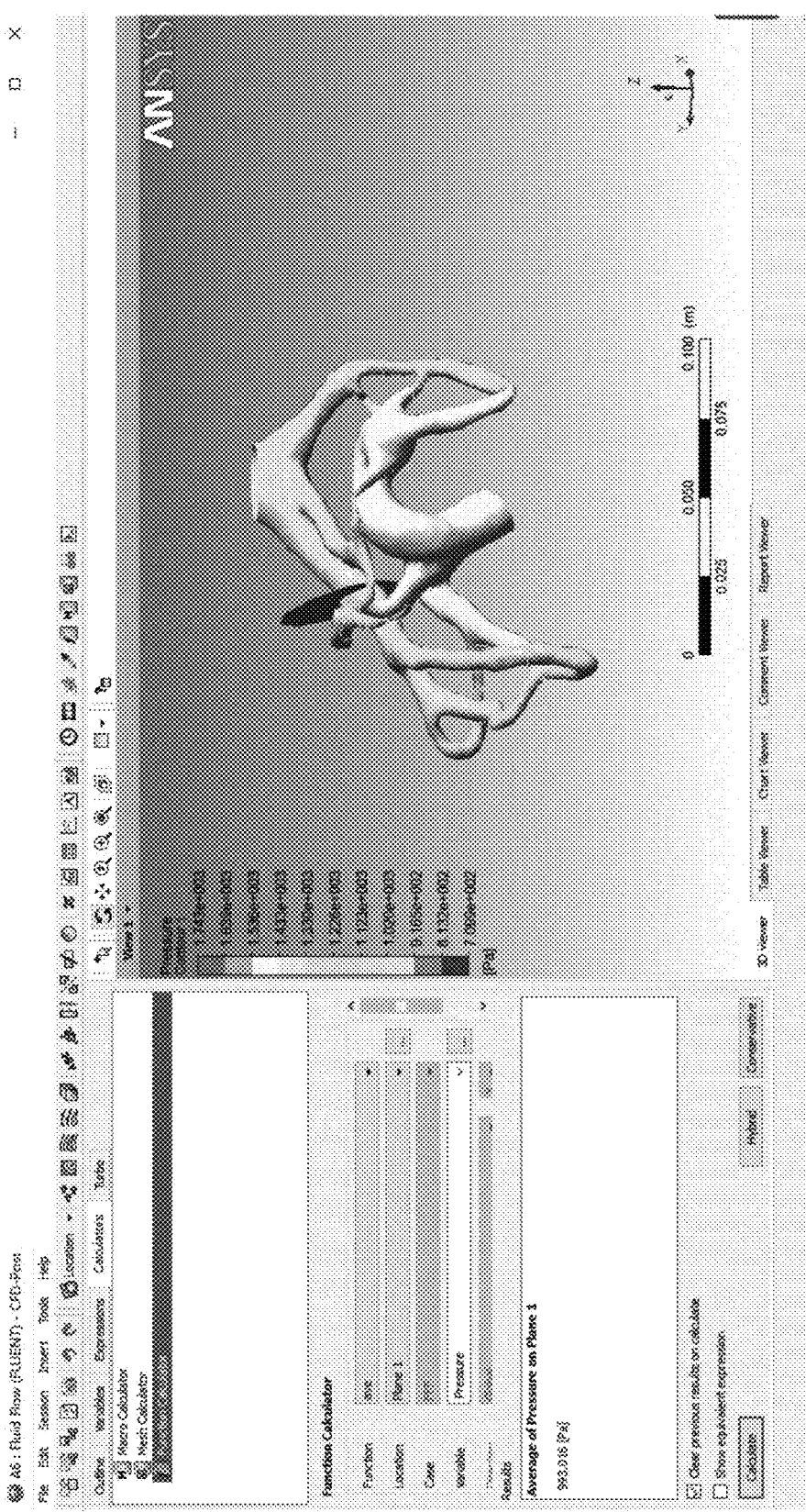
FIG. 33 shows reading of vFHVP.

10. The vFHVP was read from a panel that was used to simulate the location where the free hepatic venous pressure (FHVP) was measured in clinical practice (FIGS. 32 and 33).

Figure 34:
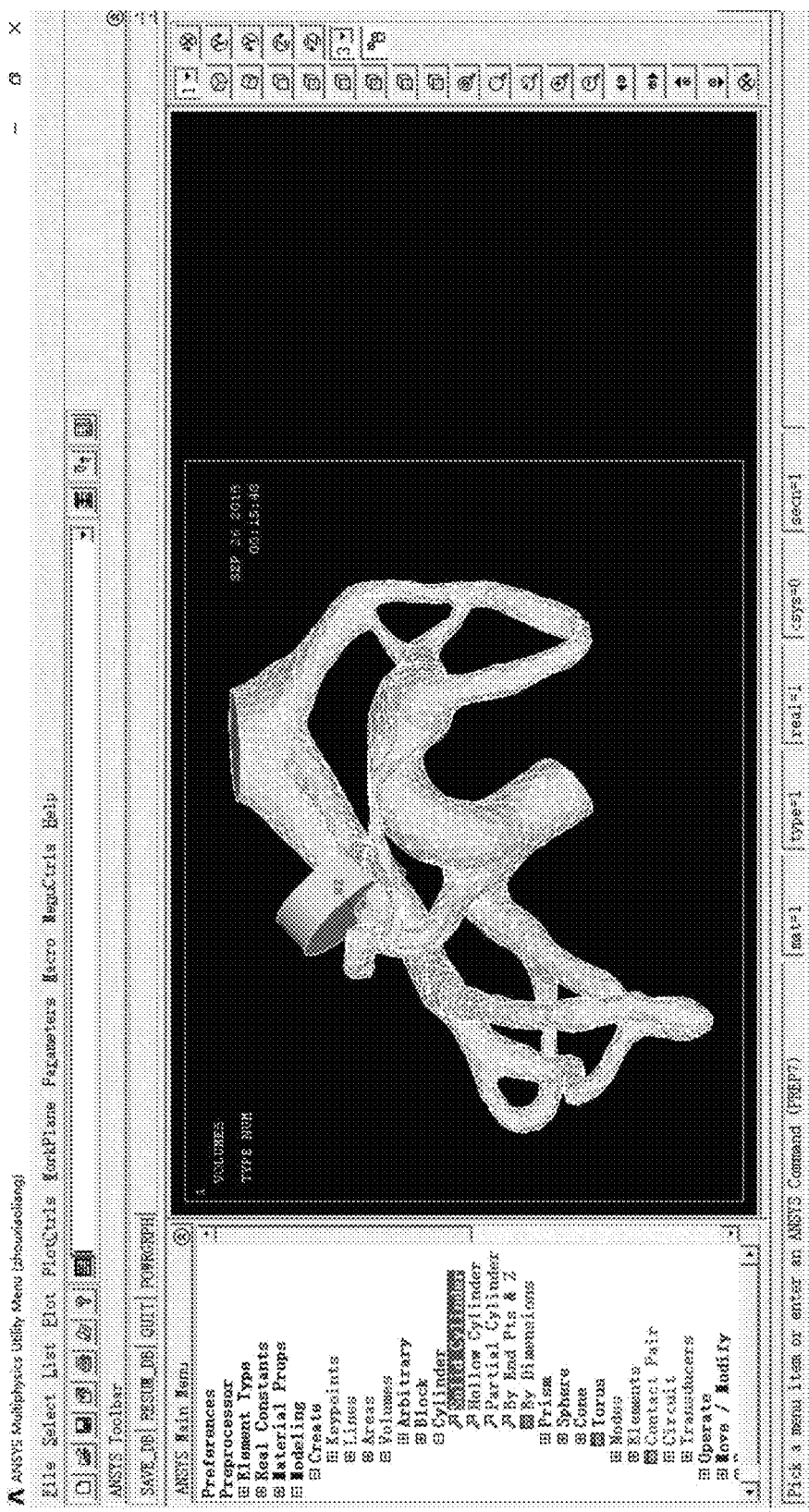
FIG. 34 shows use of a cylinder to simulate a sacculus which blocks the right hepatic vein.
Figure 35:
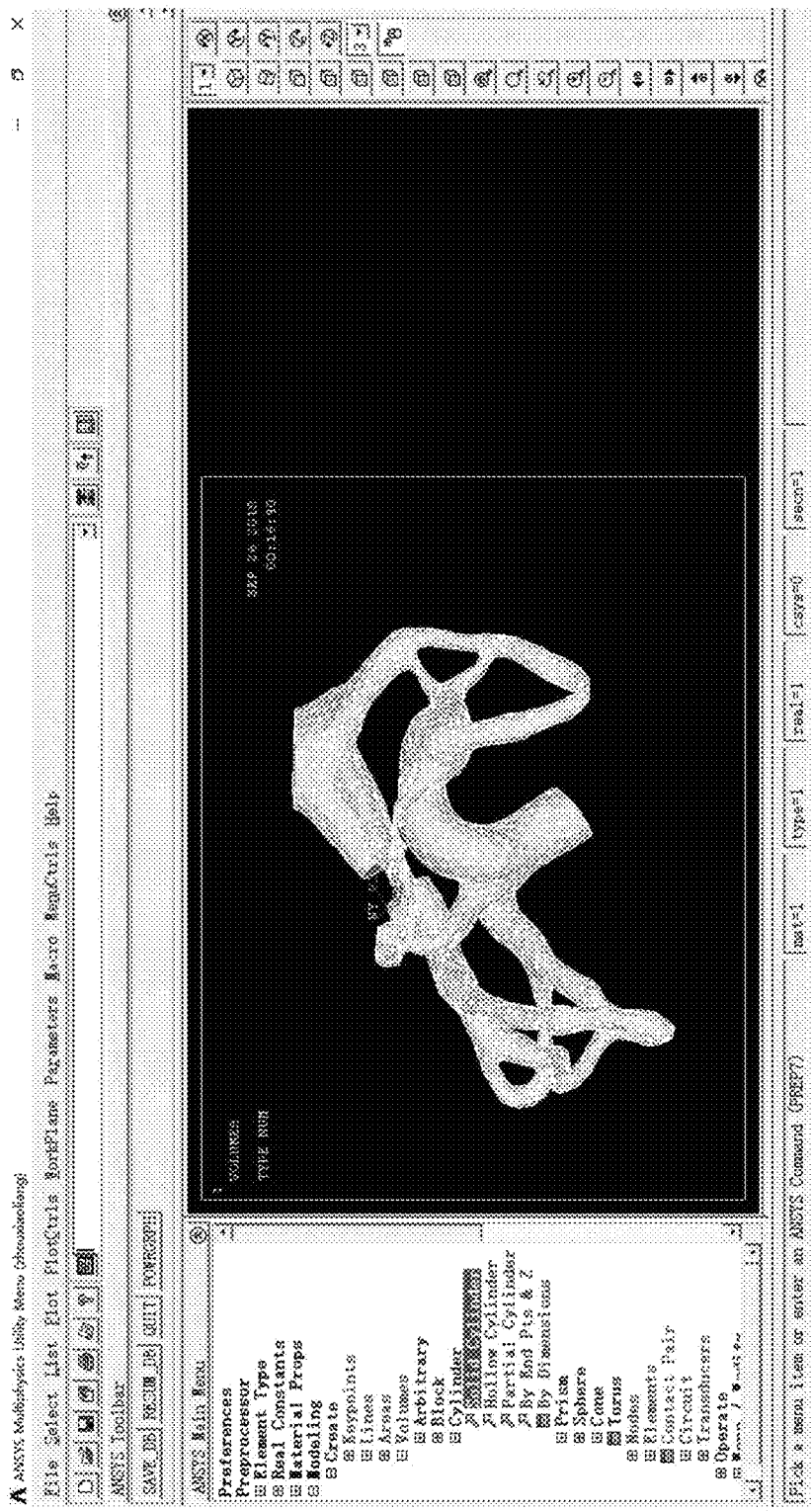
FIG. 35 shows WHVP model.
Figure 36:
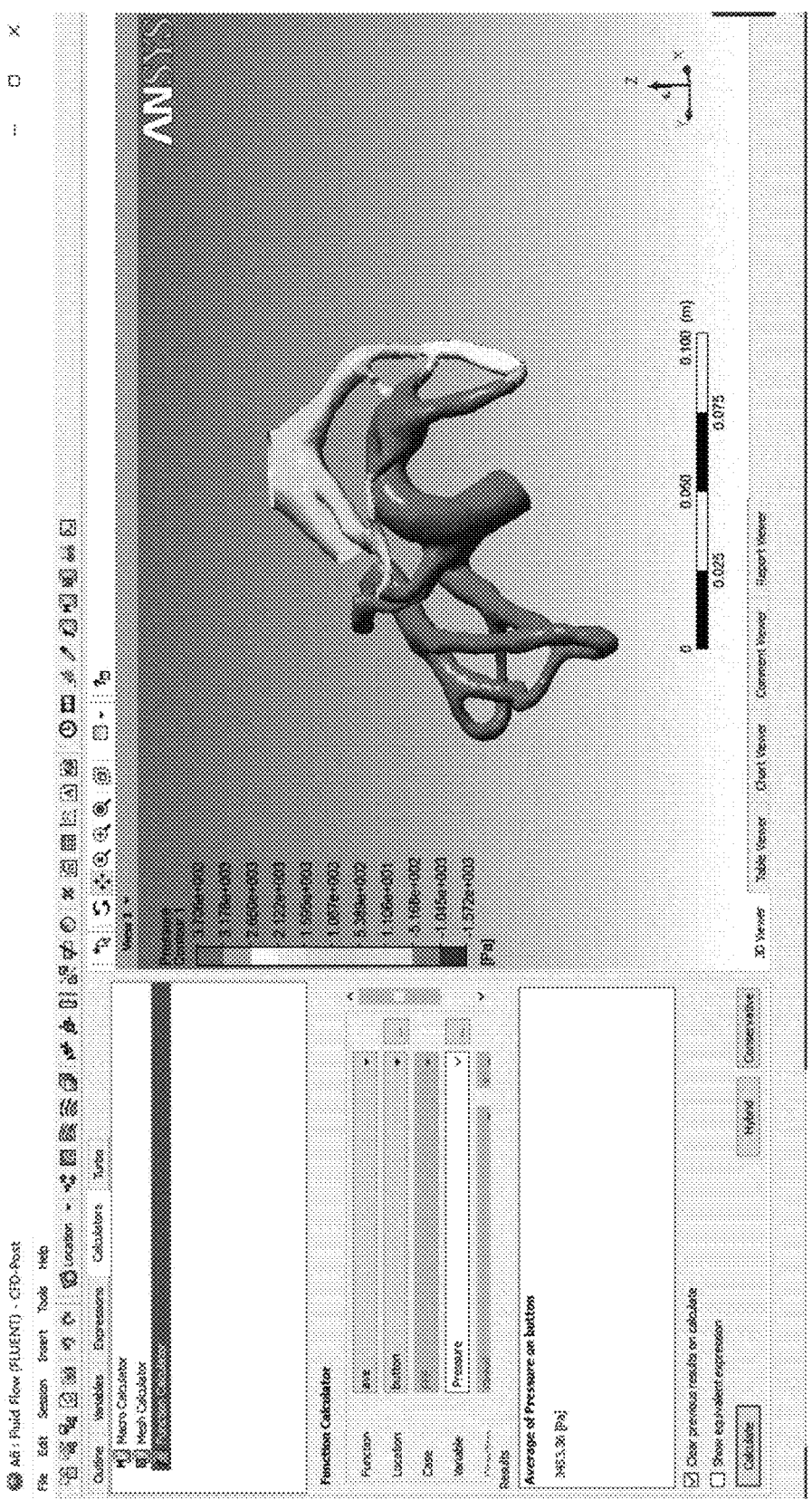
FIG. 36 shows reading of vWHVP.

11. A cylinder with a diameter greater than or equal to that of the truncated blood vessel was created to simulate an occlusion sacculus, the right hepatic vein is blocked by Boolean operation to obtain an open geometric model of the virtual wedged hepatic venous pressure (vWHVP) (FIGS. 34 and 35), which was exported as an IGS file for use (referring to step F); the IGS file was imported into the ANSYS workbench, the generated two sections were endowed with a velocity of 0 m/s to simulate blood flow stasis and the other material parameters, boundary conditions and solution control parameters were kept unchanged, the vWHVP was obtained by calculation, and the vWHVP was read in the results module (FIG. 36).

12. vHVPG was the difference between the vWHVP and the vFHVP.

Example: Fluid Dynamics Simulation Calculation of vHVPG

Figure 37:
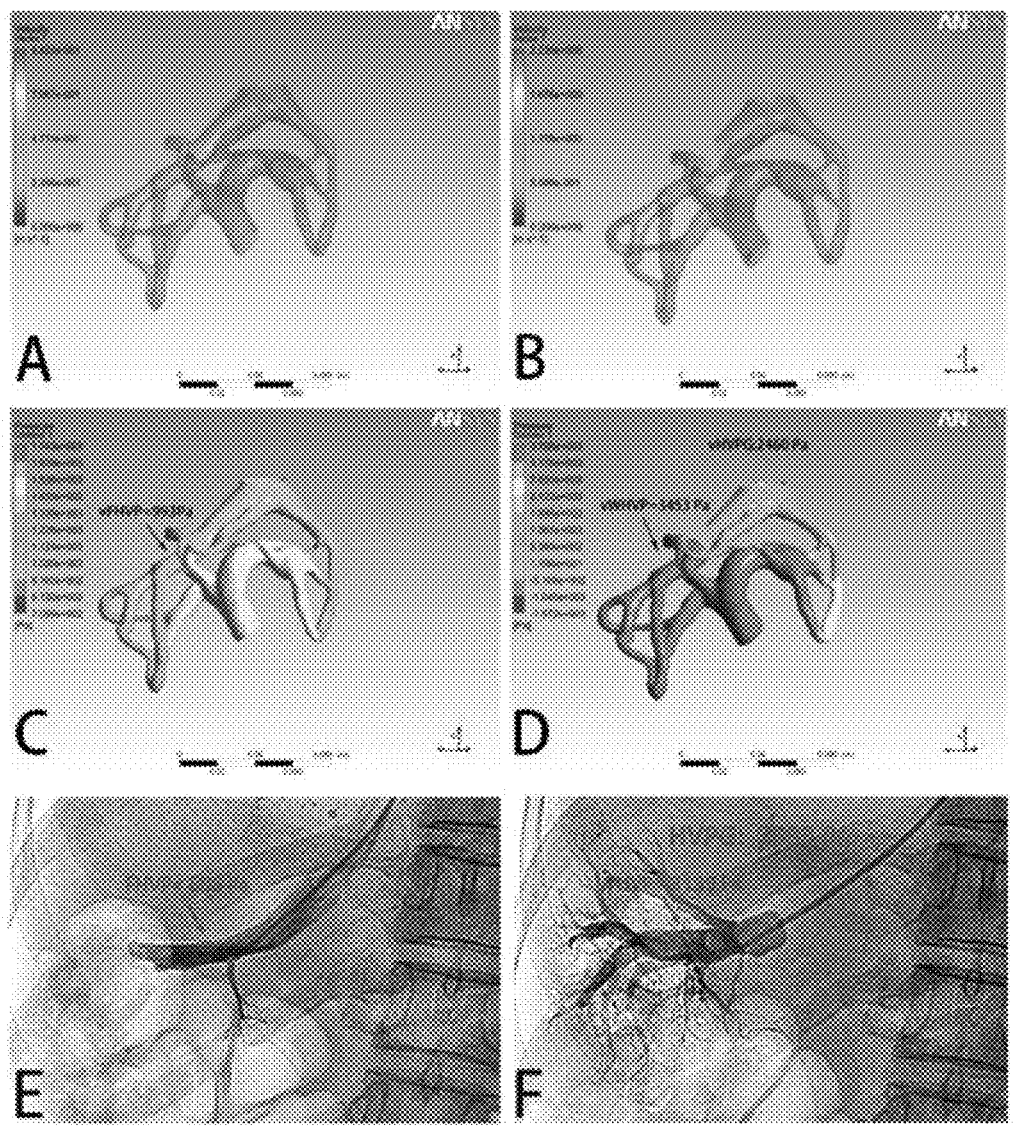
FIG. 37 is a graph showing the results of comparison between vHVPG obtained by fluid dynamics simulation calculation and the pressure measured invasively.

In the fluid dynamics simulation module Fluent, material parameters are set as follows: blood density=1050 kg/m$^3$, blood viscosity=0.005 kg/ms, and blood vessel wall density=1150 kg/m$^3$. The control parameters (calculating the step size, the number of iterations, the maximum number of cycles) and boundary conditions (blood flow velocity) are solved, "fluid-solid coupling" between the blood vessel wall and the blood is simulated, and the blood streamline distribution of vFHVP and vWHVP is simulated (FIGS. 37A and 37B).

Through the analysis and calculation by the post-processing module, a vFHVP and a vWHVP are obtained, which are 993 Pa and 3453 Pa, respectively (FIGS. 37C and 37D), and vHVPG=2460 Pa is obtained by calculating the deviation value therebetween.

According to the pressure measured invasively during transjugular intrahepatic portosystemic shunt in this case, FHVP and WHVP are 606 Pa and 3139 Pa, respectively (FIGS. 37E and 37F), and HVPG=2533 Pa can be obtained by calculation.

Figure 38:
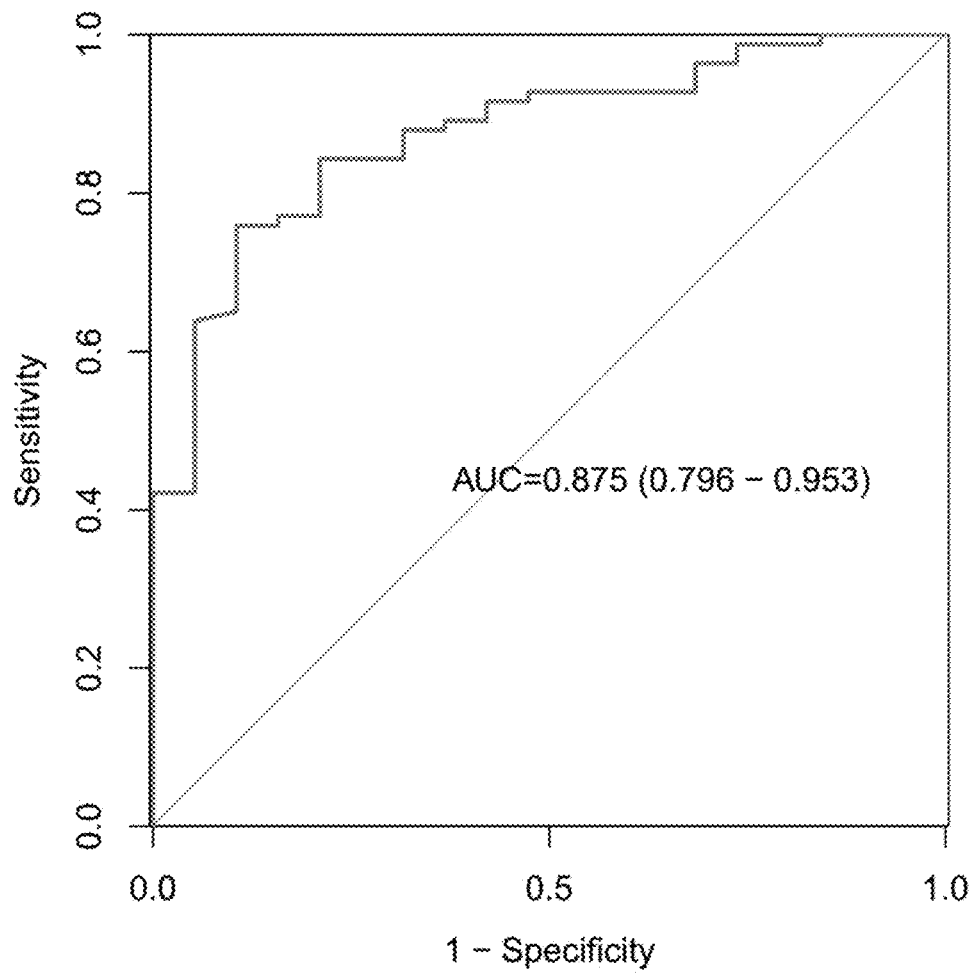
FIG. 38 shows the receiver operating characteristic (ROC) curve of vHVPG and invasive gold-standard HVPG.
Figure 39:
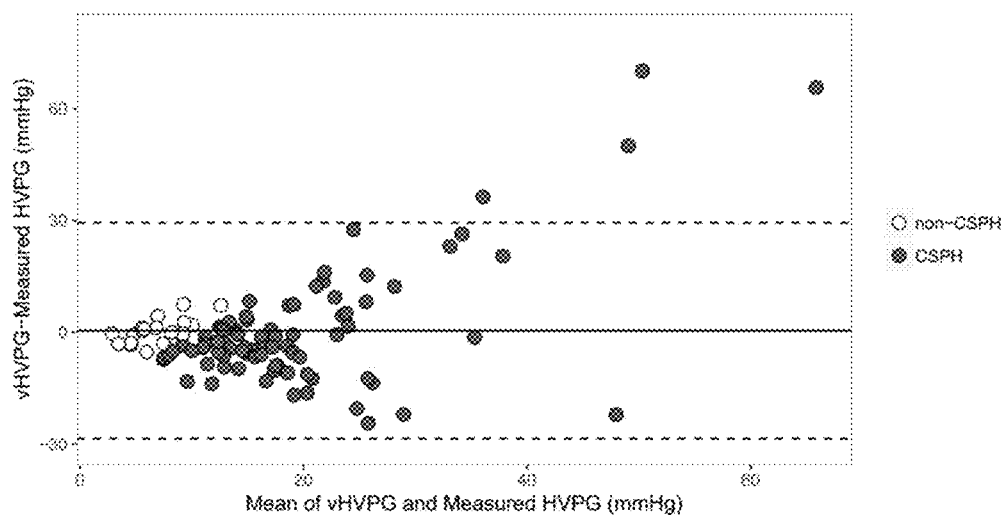
FIG. 39 is a Bland-Altman plot of consistency test between vHVPG and invasive gold-standard HVPG.
Figure 40:
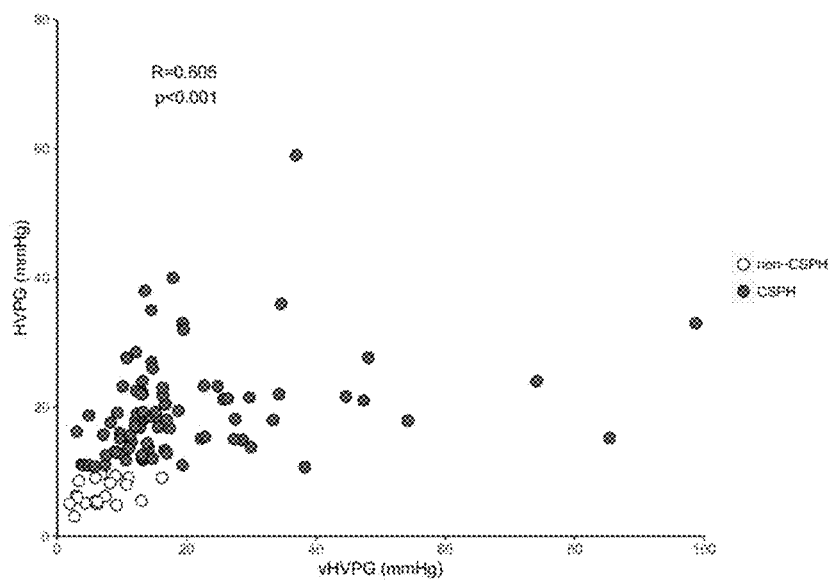
FIG. 40 is a graph of bivariate correlation of vHVPG and invasive gold-standard HVPG.

Statistical analysis is further carried out with the clinical diagnostic test data, and the results show that:

when the invasive HVPG is taken as the gold standard and the threshold is 10 mmHg (sample size: 102), the area under the ROC curve (AUC) of vHVPG is 0.886 (FIG. 38); when the invasive HVPG is taken as the gold standard (sample size: 102), the Bland-Altman plot of consistency test suggests a good agreement between vHVPG and HVPG (FIG. 39), and the bivariate correlation scatter plot suggests that the Spearman correlation coefficient between vHVPG and HVPG is 0.605, p<0.001 (FIG. 40).

The statistical analysis shows that the vHVPG in the present disclosure is of relatively high diagnostic value when the invasive HVPG value is used as a reference standard. The invasive HVPG has been incorporated into the gold standards recommended by the international guidelines. The non-invasive determination method of the present disclosure can overcome the problems that the reference standard in the early stage is not ideal and is easily interfered by general anesthesia laparotomy. Therefore, the new non-invasive vHVPG determination technique proposed in the present disclosure is feasible, can comprehensively evaluate the diagnostic value of the vHVPG, is expected to provide a new idea for the non-invasive diagnosis of cirrhotic portal hypertension and plays a positive role in improving the quality of life of patients suffering from portal hypertension and reducing the disease burden of families and society.

Computational fluid dynamics is an effective way to solve fluid computing problems. The main method thereof is finite element analysis: arbitrarily dividing a continuous solution domain into many tiny elements with appropriate shapes and constructing interpolation functions in each small element separately, converting, according to the extremum principle (variational or weighted residual method), the governing equation of the problem into finite element equations on all the elements, setting the global extremum as the sum of the extremums of all the elements, integrating the local elements to form an algebraic equation set embedded with specified boundary conditions, and solving the set of equations to obtain the function value of each node. The basic equation of fluid calculation is Navier-Stokes equation, which can be written in rectangular coordinates as:

$$\rho \frac{du}{dt} = -\frac{\partial p}{\partial x} + \rho X + \mu \Delta u$$
$$\rho \frac{dv}{dt} = -\frac{\partial p}{\partial y} + \rho Y + \mu \Delta v,$$
$$\rho \frac{dw}{dt} = -\frac{\partial p}{\partial z} + \rho Z + \mu \Delta w$$

wherein $\Delta$ indicates Laplace operator, $\rho$ indicates fluid density, p indicates pressure, u, v, w indicate velocity components of the fluid at points (x, y, z) at time t, X, Y, Z indicate components of an external force, and the constant $\mu$ indicates a dynamic viscosity coefficient. The actual deformation amount of the blood vessel wall in the hepatic vein-portal vein system is relatively small, the blood viscosity in the blood vessel is relatively low and can be regard as a constant viscosity (the internal friction shear force of the fluid is approximately linear with the relative speed between the two fluids at the unit distance), and the blood density is approximately constant. Therefore, the blood in the hepatic vein-portal vein system can be approximated as incompressible Newtonian fluid. The non-dimensional parameter that determines whether the motion state of fluid is laminar or turbulent is Reynolds number (Re), which is defined as Re=$\rho$VD/$\mu$ ($\rho$ indicates fluid density, V indicates fluid velocity, D indicates inner diameter, and $\mu$ indicates fluid viscosity). When Re<2000, the fluid is laminar, and when Re>3000, it is turbulent. It can be obtained by calculation that the blood in the hepatic vein-portal vein system is in laminar motion.

The invention claimed is:

1. A method for determining a virtual hepatic venous pressure gradient (vHVPG) comprising:
   A. injecting a contrast agent through a median cubital vein of a specimen;
     (iA) performing a CT angiography (CTA) to acquire a CTA slice sequence including hepatic venous phase; and
     (iiA) exporting the slice sequence, with a format of dicom, a slice thickness of 1.25 mm and an image resolution of 512×512 pixels;
   B. importing the acquired CTA slice sequence into a medical image control software MIMICS;
     (iB) selecting a slice sequence in a hepatic venous phase;
     (iiB) setting an orientation of an image sequence; and
     (iiiB) automatically recognizing the image sequence by the software MIMICS to generate coronal, sagittal and horizontal images of the CTA image sequence in the hepatic venous phase;
   C. searching for a hepatic vein-portal vein system, which is a target, in each image;
     (iC) reconstructing hepatic and portal vein trees by using hepatic venous phase images with a soft tissue window;
     (iiC) segmenting a hepatic-venous system from surrounding liver parenchyma by using thresholding technique based on Hounsfield units;
     (iiiC) then saving masking of the selected hepatic-portal venous region by using crop mask;
     (iiiiC) selecting the target using a Region growing tool of the software MIMICS so as to only extract a structure connected with the target in spatial structure; and (vC) establishing a preliminary 3D hepatic vein-portal vein model by using a Calculate-3D-from-mask tool of the software MIMICS and selecting medium quality which is of medium precision;
   D. eliminating residual non-target structures and only retaining a hepatic vein-portal vein system by using an Edit-masks-in-3D tool of the software MIMICS; and
     (iD) further selectively filling the hepatic vein-portal vein system and eliminating noise pixels by repeatedly using the Edit-masks-in-3D tool and a 2D Edit mask tool of the software MIMICS, so as to reconstruct a solid 3D model of the hepatic vein-portal vein system with a lumen being closed;
   E. remeshing the model with the quality-threshold of 0.01 by using remesh technique (split-based method);
     (iE) smoothing the hepatic-portal venous model by using a Smooth tool; then (iiE) outputting the model with a format of an Ansys area file (.lis);
   F. importing area element, with the format of the .lis, in classic mode of ANSYS, and (iF) unifying a unit of the length as an international unit m; and
(iiF) establishing a solid model of the hepatic vein-portal vein system model on the basis of an area;
G. making a vertical section of blood inlet and outlet of the hepatic vein-portal vein system model by Boolean operation, to obtain an open geometric model of virtual free hepatic venous pressure (vFHVP); and thereafter exporting a file with a suffix .IGS for use, wherein IGS is a file format of 3D numerical model, which is readable by ANSYS Workbench module;
H. establishing an ANSYS Workbench finite element calculation platform, including a geometrical model module Geometry, a fluid calculation module Fluent and a Results module, which is a CFD-POST post-processing module,
(iH) importing an IGS file through Geometry module, in a Mesh unit, wherein objects of meshing being imported undergo numerical models and a meshing method being set as Tetrahedrons;
(iiH) selecting Computational Fluid Dynamics (CFD) in a Physics Preference, and (iiiH) selecting a Fluent in a Solver Preference, (iiiiH) solving the flow field using the Fluent; (vH) defining a mesh size in consideration of operation accuracy and a running speed of a computer, setting a max face size to 1.5 mm and a max size to 4 mm;
(viH) thereafter accomplishing meshing through Generate Mesh;
I. setting material parameters, comprising a blood density, a blood viscosity and a blood vessel wall density, in solution of fluid dynamics calculation module Fluent to make physical properties of the model close to biological properties of human body so as to improve accuracy of a simulation;
(iI) solving control parameters, including step size, number of iterations, and maximum number of cycles and boundary conditions, including naming a surface of the blood inlet and providing therefor a velocity value for the surface of the blood inlet, naming a surface of the outlet and then providing a pressure value for the surface of the outlet, and setting an unnamed blood vessel wall as wall, Reynolds number of portal vein flow being $Re<2000$, so that simulation fluid is set as a laminar flow;
(iiI) setting operation initialization to start from an inlet surface; and
(iiiI) simulating fluid-solid coupling between a blood vessel wall and blood after completion of parameter setting, and obtaining, by calculation, a pressure distribution and blood flow distribution of a simulation 3D blood vessel model;
J. reading results in a results module which is of post-processing, and displaying a map of the pressure distribution of liver-portal vein model through contour operation; and acquiring, by calculation, a numerical value of the virtual free hepatic venous pressure (vFHVP) by using a tab provided by a software, which is called as calculators;
K. creating a cylinder with a diameter greater than or equal to that of a truncated blood vessel to simulate an occlusion sacculus, blocking right hepatic vein by Boolean operation to obtain an open geometric model of virtual wedged hepatic venous pressure (vWHVP), which is exported as an IGS file for use, as indicated in Step F; (iK) importing the IGS file into the ANSYS workbench, endowing two generated sections with a velocity of 0 m/s to simulate blood flow stasis and keeping other material parameters, boundary conditions and solution control parameters unchanged, obtaining, by calculation, the virtual wedged hepatic venous pressure (vWHVP), and reading the virtual wedged hepatic venous pressure (vWHVP) in the results module; and
L. calculating a deviation value between the vWHVP and the vFHVP, which is virtual hepatic venous pressure gradient (vHVPG).

2. The method for determining the virtual hepatic venous pressure gradient according to claim 1, wherein the material parameters are set as follows in step I: blood density=1050 kg/m$^3$, blood viscosity=0.005 kg/m·s, and blood vessel wall density=1150 kg/m$^3$.

* * * * *